United States Patent [19] [11] 3,931,407
Allen et al. [45] Jan. 6, 1976

[54] METHOD OF TREATMENT WITH AND COMPOSITIONS CONTAINING CONDENSED PYRROLES BEARING AN N-PHENYL SUBSTITUENT

[75] Inventors: Richard C. Allen, Somerville; V. Brian Anderson, High Bridge, both of N.J.

[73] Assignee: American Hoechst Corporation, Somerville, N.J.

[22] Filed: Oct. 31, 1974

[21] Appl. No.: 519,844

Related U.S. Application Data

[62] Division of Ser. No. 336,919, March 1, 1973, Pat. No. 3,878,225.

[52] U.S. Cl. .................................................. 424/274
[51] Int. Cl.[2] ........................................ A61K 31/40
[58] Field of Search .................................. 424/274

[56] References Cited
UNITED STATES PATENTS
3,687,971   8/1972   Shen et al. ................... 260/302 X Primary Examiner—Stanley J. Friedman
Attorney, Agent, or Firm—Curtis, Morris & Safford

[57] ABSTRACT

Novel N-phenylpyrroles are disclosed that are effective in the treatment of inflammation and pain in mammals and have the formula

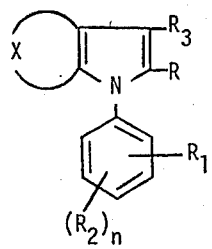

wherein
R is hydrogen, alkyl of one to six carbon atoms, thienyl, phenyl or phenyl substituted by halogen, trifluoromethyl, alkyl of one to six carbon atoms, alkoxy of one to six carbon atoms, alkanoyloxy of one to six carbon atoms, alkanoylamino of one to six carbon atoms, nitro, cyano, hydroxyl, amino or phenyl;
$R_1$ is carboxyl, alkoxycarbonyl of two to seven carbon atoms, carbamoyl, N-alkylcarbamoyl of two to seven carbon atoms, N,N-dialkylcarbamoyl of three to seven carbon atoms, hydroxycarbamoyl or dialkylphosphinylalkoxycarbonyl of four to 10 carbon atoms;
$R_2$ is hydrogen, hydroxyl, mercapto, halogen, trifluoromethyl, alkyl of one to six carbon atoms, alkoxy of one to six carbon atoms, alkanoyloxy of one to six carbon atoms, alkylthio of one to six carbon atoms, amino, alkylamino of one to six carbon atoms, dialkylamino of two to six carbon atoms, alkanoylamino of one to six carbon atoms, alkanoylthio of one to six carbon atoms, thiocarbamoyloxy, alkylthiocarbamoyloxy of two to six carbon atoms, dialkylthiocarbamoyloxy of three to seven carbon atoms, carbamoylthio, alkylcarbamoylthio of one to six carbon atoms, dialkylcarbamoylthio of two to seven carbon atoms, carbamoylamino, alkylcarbamoylamino of two to six carbon atoms or dialkylcarbamoylamino of three to seven carbon atoms;
$R_3$ is hydrogen, alkanoyl of one to six carbon atoms, or phenyl;
X is alkylene of three to five carbon atoms, alkylene of three to five carbon atoms substituted by alkyl or alkoxy of one to six carbon atoms, divinylene, divinylene substituted by alkyl of one to six carbon atoms,

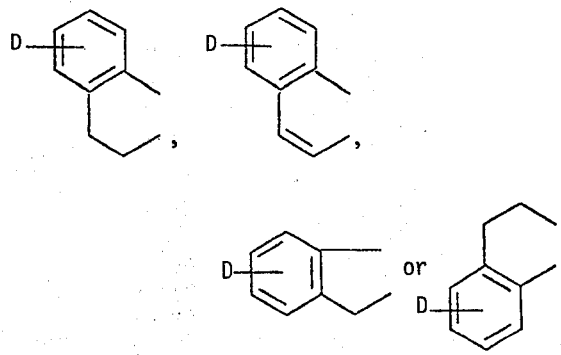

wherein D is hydrogen, alkyl of one to six carbon atoms, alkoxy of one to six carbon atoms, alkanoyloxy of one to six carbon atoms, alkanoylamino of one to six carbon atoms, halogen, amino, nitro or trifluoromethyl; and n is 1 or 2.

24 Claims, No Drawings

METHOD OF TREATMENT WITH AND COMPOSITIONS CONTAINING CONDENSED PYRROLES BEARING AN N-PHENYL SUBSTITUENT

This is a division of application Ser. No. 336,919 filed Mar. 1, 1973, now U.S. Pat. No. 3,878,225 granted Apr. 15, 1975.

This invention relates to novel N-phenylpyrroles having anti-inflammatory and analgesic activity, to methods of preparing the same and to a method of treatment therewith for reducing inflammation and pain in mammals.

German Offenlegungsschrift No. 1,938,904 relates to N-arylpyrroles of the formula

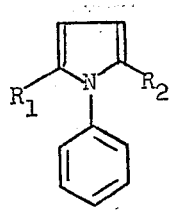

in which $R_1$ and $R_2$ are methyl-, phenyl-, methylphenyl- or halogenated phenyl and the N-phenyl group may carry one or two substituents. These compounds are described to be useful as anti-inflammatory and analgesic agents.

We have found a genus of N-phenylpyrroles having superior anti-inflammatory and analgesic activity, and minimal side effects. These are compounds of the formula

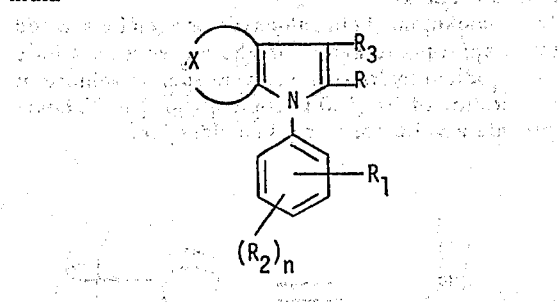

wherein

R is hydrogen, alkyl of one to six carbon atoms, thienyl, phenyl or phenyl substituted by halogen, trifluoromethyl, alkyl of one to six carbon atoms, alkoxy of one to six carbon atoms, alkanoyloxy of one to six carbon atoms, alkanoylamino of one to six carbon atoms, nitro, cyano, hydroxyl, amino or phenyl;

$R_1$ is carboxyl, alkoxycarbonyl of two to seven carbon atoms, carbamoyl, N-alkylcarbamoyl of two to seven carbon atoms, N,N-dialkylcarbamoyl of three to seven carbon atoms, hydroxycarbamoyl or dialkylphosphinylalkoxycarbonyl of four to 10 carbon atoms;

$R_2$ is hydrogen, hydroxyl, mercapto, halogen, trifluoromethyl, alkyl of one to six carbon atoms, alkoxy of one to six carbon atoms, alkanoyloxy of one to six carbon atoms, alkylthio of one to six carbon atoms, amino, alkylamino of one to six carbon atoms, dialkylamino of two to six carbon atoms, alkanoylamino of one to six carbon atoms, alkanoylthio of one to six carbon atoms, thiocarbamoyloxy, alkylthiocarbamoyloxy of two to six carbon atoms, dialkylthiocarbamoyloxy of three to seven carbon atoms, carbamoylthio, alkylcarbamoylthio of one to six carbon atoms, dialkylcarbamoylthio of two to seven carbon atoms, carbamoylamino, alkylcarbamoylamino of two to six carbon atoms or dialkylcarbamoylamino of three to seven carbon atoms;

$R_3$ is hydrogen, alkanoyl of one to six carbon atoms, or phenyl;

X is alkylene of three to five carbon atoms, alkylene of three to five carbon atoms substituted by alkyl or alkoxy of one to six carbon atoms, divinylene, divinylene substituted by alkyl of one to six carbon atoms,

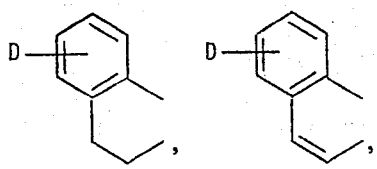

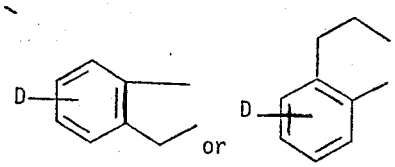

wherein D is hydrogen, alkyl of one to six carbon atoms, alkoxy of one to six carbon atoms, alkanoyloxy of one to six carbon atoms, alkanoylamino of one to six carbon atoms, halogen, amino, nitro or trifluoromethyl; and n is 1 or 2.

The compounds that are preferred are those in which R is alkyl of one to six carbon atoms, thienyl, phenyl, diphenyl of phenyl substituted by halogen, trifluoromethyl, alkyl of one to six carbon atoms, alkoxy of one to six carbon atoms, nitro, cyano or hydroxy;

$R_2$ is hydrogen, hydroxyl, mercapto, halogen, trifluoromethyl, alkoxy of one to six carbon atoms, alkanoyloxy of one to six carbon atoms, amino, alkanoylamino of one to six carbon atoms, dialkylthiocarbamoyloxy of three to seven carbon atoms or dialkylcarbamoylthio of three to seven carbon atoms; and D is hydrogen, alkoxy of one to six carbon atoms or halogen are particularly desirable as are compounds in which R is a tertiary butyl, thienyl, phenyl, diphenyl or phenyl substituted by chlorine, bromine, fluorine, hydroxyl, trifluoromethyl, methyl, methoxy, nitro or cyano;

$R_1$ is carboxyl, methoxycarbonyl, ethoxycarbonyl, carbamoyl, N-ethylcarbamoyl, N,N-diethylcarbamoyl, hydroxycarbamoyl or dimethylphosphinylmethoxycarbonyl;

$R_2$ is hydrogen, hydroxyl, mercapto, chlorine, bromine, trifluoromethyl, methoxy, acetyl, acetylamino, dimethylthiocarbamoyloxy or dimethylcarbamoylthio;

$R_3$ is hydrogen, acetyl or phenyl; and

X is X alkylene of three to five carbon atoms, butylene substituted by methyl, tertiary butyl or methoxy, divinylene, divinylene substituted by tertiary butyl,

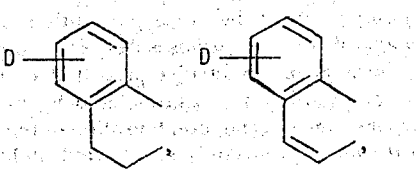

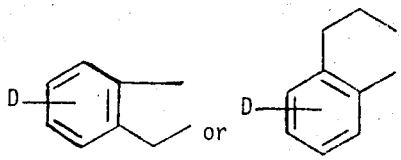

wherein D is hydrogen, methoxy or chlorine.

Optimum results have been obtained with
3-(3-carboxy-4-hydroxyphenyl)-4,5-dihydro-2-phenylbenz[e]indole, 3-(4-acetoxy-3-carboxyphenyl)-4,5-dihydro-2-phenylbenz[e]indole,
3-(3-carboxy-4-hydroxyphenyl)-2-phenylbenz[e]indole,
1-(3-carboxy-4-hydroxyphenyl)-2-phenylindole, and
1-(3-carboxy-4-hydroxyphenyl)-2-phenyl-4,5,6,7-tetrahydroindole.

The compounds of the present invention are obtainable by any of several syntheses described immediately below. These generally involve, as a first step, the formation of a γ-diketone, γ-ketoaldehyde, or β-acetylenic ketone, and second, condensation of this intermediate with an appropriately substituted aniline in the presence of an acid catalyst. In the case of fully aromatic compounds, the second step is followed by an aromatization reaction.

Methods A and B:

An α-haloketone, ketal, aldehyde or acetal is condensed with an enamine of an appropriate ketone in a solvent such as dimethylformamide or toluene at a temperature of 0° to 120°C. for a time of 1 hour to 72 hours, followed by hydrolysis at a temperature of 25 to 100°C. for a period of 1 to 24 hours, to provide a γ-diketone or γ-ketoaldehyde.

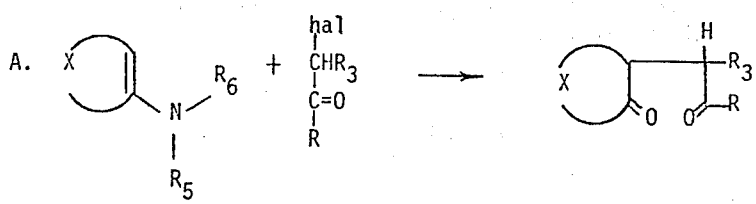

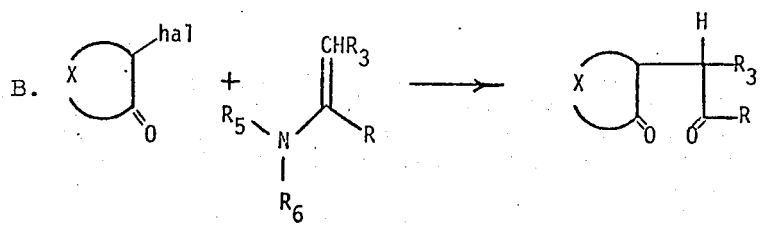

Methods C and D:

An α-haloketone, ketal, aldehyde or acetal is reacted with an appropriate ketone in the presence of a base such as sodium hydride in a solvent such as toluene at a temperature of 70°–120°C. for a time of 1 to 72 hours to provide a γ-diketone or γ-ketoaldehyde.

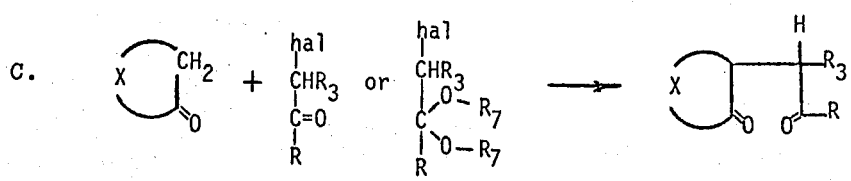

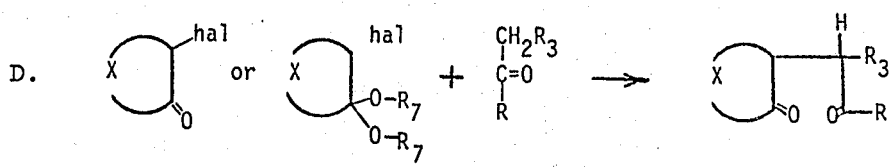

Method E:

A sterically hindered β-ketoalkanoate is treated with an α-haloketone, ketal, aldehyde or acetal in the presence of a base such as sodium hydride in a solvent such as dimethylformamide or toluene at a temperature of 0° to 110°C. for a period of 1 to 24 hours followed by acid hydrolysis to provide a γ-diketone or γ-ketoaldehyde.

E. 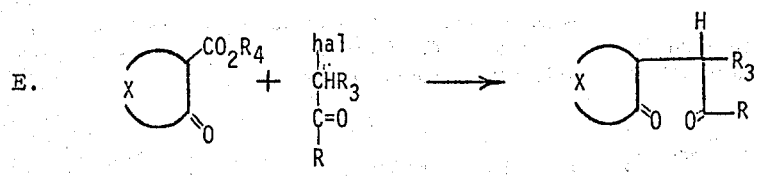

Method F:
A β-ketosulfoxide is treated with an α-haloketone, ketal, aldehyde, or acetal in the presence of a base such as sodium hydride in a solvent such as dimethylsulfoxide at a temperature of 0° to 100°C. for a period of 1 to 24 hours followed by reduction with a reagent such as aluminum amalgam in a solvent such as aqueous tetrahydrofuran, to provide a γ-diketone or γ-ketoaldehyde.

F. 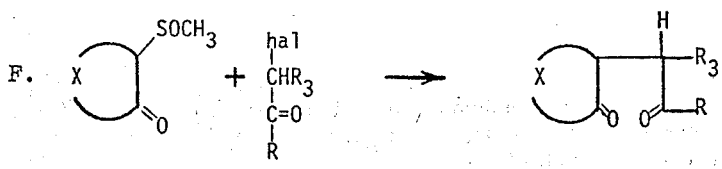

Method G:
A 1,2-disubstituted-1-nitroethylene is treated with an appropriate ketone in the presence of a base such as sodium hydroxide in the presence of a solvent such as water at a temperature of 25° to 100°C for a period of 1 minute to 3 hours, followed by acidification with an acid such as acetic acid and heating from 50° to 100°C. in a solvent such as methanol for a period of 1 to 10 hours to provide a γ-diketone or γ-ketoaldehyde.

G. 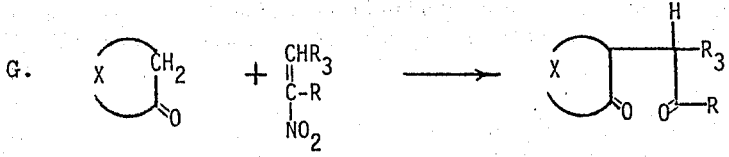

Method H:
An enol lactone of a γ-ketocarboxylic acid is treated with an N,N-dialkylynamine in a solvent such as acetonitrile at a temperature of 25° to 100°C. for a period of 1 minute to 5 hours followed by acid hydrolysis to provide a γ-diketone or γ-ketoaldehyde.

H. 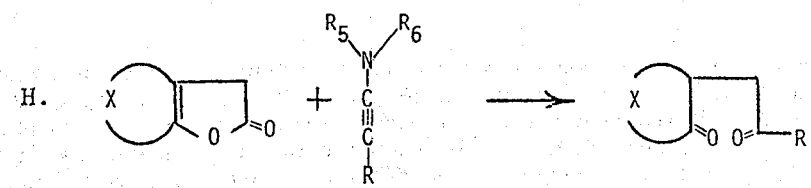

Method I:
An appropriately substituted furan is treated with bromine in the presence of a base such as sodium carbonate at a temperature of −10° to 10°C. in a solvent such as methanol followed by hydrogenation at a pressure of 1 to 2 atmospheres with a catalyst such as 5% Pd on CaCO₃ for a period of 1 to 24 hours with subsequent acid hydrolysis, to provide a γ-diketone or γ-ketoaldehyde.

I. 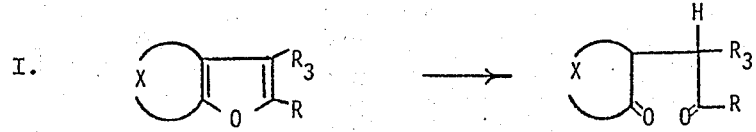

Method J:
An enamine of an appropriate ketone is condensed with a substituted α-haloacetylene in a solvent such as dimethylformamide at a temperature of 0° to 100°C. for a period of 1 to 72 hours, followed by hydrolysis at a temperature of 25° to 100°C. for a period of 1 to 6 hours and treated with a reagent such as mercurated Amberlite IR 120 resin in a solvent such as methanol at a temperature of 25° to 75°C. for a period of 1 to 10 hours, to provide a γ-diketone.

J. 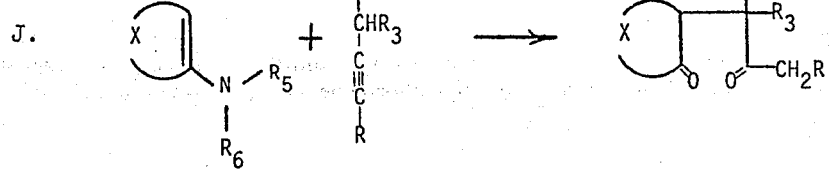

Method K:

An appropriate ketone is condensed with a substituted α-haloacetylene in the presence of a base such as

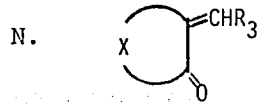 + 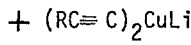 → 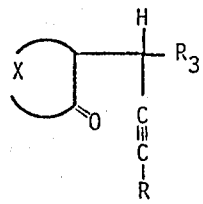

potassium t-butoxide in a solvent such as t-butanol for a period of 1 to 10 hours at a temperature of 25° to 100°C followed by treatment with a reagent such as mercurated Amberlite IR 120 resin in a solvent such as methanol at a temperature of 25° to 75°C for a period of 1 to 10 hours, to provide a γ-diketone.

solvent such as tetrahydrofuran at a temperature of −100° to −50°C. for a period of 1 to 24 hours, to provide a β-acetylenic ketone.

In the foregoing schematically illustrated reactions, $R$, $R_1$, $R_2$, $R_3$ and $X$ are as hereinbefore defined; hal is chlorine, bromine or iodine; $R_5$ and $R_6$ are the same or different alkyl groups of one to six carbon atoms each so fused to form, with the nitrogen atom to which they are attached, a cyclic secondary amine having a five to K. 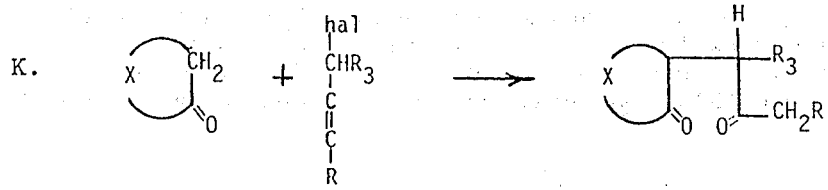

Method L:

An enamine of an appropriate ketone is condensed with a substituted α-haloacetylene in a solvent such as dimethylformamide at a temperature of 0° to 100°C for a period of 1 to 72 hours followed by hydrolysis at a temperature of 25° to 100°C for a period of 1 to 6 hours, to provide a β-acetylenic ketone.

six membered ring such as pyrrolidine, morpholine or piperidine; $R_7$ is alkyl of one to six carbon atoms or both $R_7$s of a

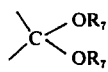

L. 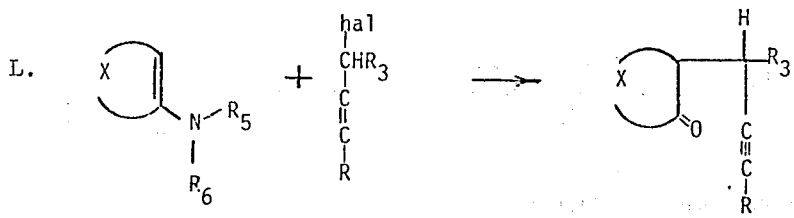

Method M:

An appropriate ketone is treated with a substituted α-haloacetylene in the presence of a base such as potassium t-butoxide in a solvent such as t-butanol for a period of 1 to 10 hours at a temperature of 25° to 100°C. to provide a β-acetylenic ketone.

group are fused to form a chain of two or three carbon atoms; $R_4$ is a branched or cyclic alkyl of four to eight carbon atoms. For the second step in the reaction sequence, a γ-diketone or γ-ketoaldehyde is reacted with an appropriately substituted aniline under acidic conditions in a solvent such as acetic acid for a period of 5

M. 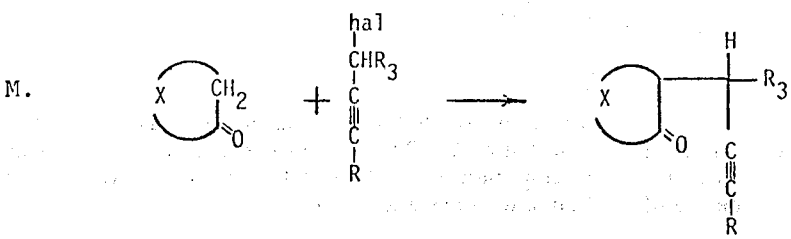

Method N:

An α,β-unsaturated ketone is reacted with a substituted diethynylcopperlithium-tributyl phosphine in a minutes to 8 hours at a temperature of 50° to 150°C. to provide a pyrrole of the present invention (Method O). Alternatively, a β-acetylenic ketone is reacted with an appropriately substituted aniline in a solvent such as ethanol for a period of 1 hour to 24 hours at a temperature of 50° to 200°C. in the presence of a catalyst such as cuprous ion to provide a pyrrole of the present invention (Method P).

laboratory procedure to assess useful anti-inflammatory activity [Proc. Soc. Exp. Biol. Med., 111, 544 (1962); J. Pharmacol. Exp. Ther., 141, 369 (1963)]. Their activity is expressed as $ED_{50}$, the dose (mg/kg) needed to produce a 50% reduction in edema as com-

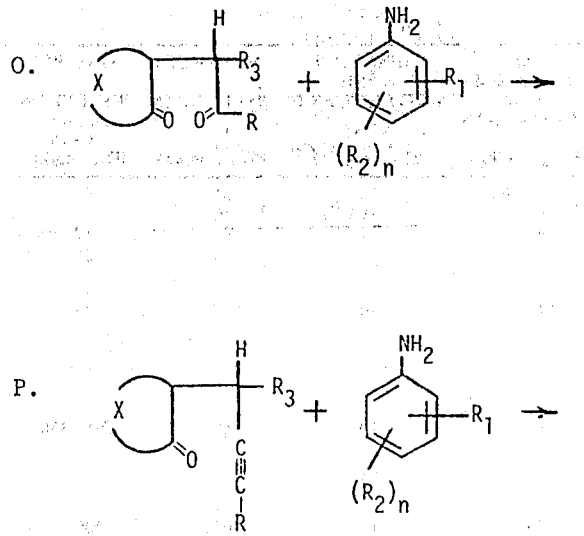

An optional third step in the reaction sequence is the aromatization of a partially saturated pyrrole of the invention by treatment with a catalyst such as 10% Pd/C in a solvent such as xylene at a temperature of 100° to 200°C. for 6 to 72 hours to form a fully aromatic pyrrole.

An aryl carboxylic group of a compound prepared according to Methods O or P ($R_1$ being carboxyl) can be reacted in known manner (a) to yield the corresponding ester (Method Q; $R_1$ being alkoxycarbonyl with one to six carbon atoms), or (b) to prepare the corresponding acyl chloride (Method R; $R_1$ being carbonyl chloride), or (c) to prepare the corresponding amide (Method T; $R_1$ being carboxamide).

Further, an aryl carboxylic acid ester group of a compound prepared according to Method O, P ($R_1$ being alkoxycarbonyl with one to six carbon atoms) can be reacted in known manner (a) with hydroxylamine to provide the corresponding hydroxamic acid (Method S; $R_1$ being hydroxycarbamoyl) or (b) with alkylamine to yield the corresponding N-alkyl amide (Method T; $R_1$ being alkylcarbamoyl with one to six carbon atoms).

Comparative tests of representative compounds of the invention with aspirin and phenylbutazone indicate that the compounds of the invention have anti-inflammatory-analgesic-antipyretic activity in mammals that makes them useful in the treatment of arthritis and other inflammatory diseases with exceptionally minimal side effects, notably gastrointestinal irritation. These conclusions follow from the data in Table 1 below.

The first column of data demonstrates the ability of the compounds of the present invention to suppress edema induced by carrageenin in rat paws, a standard pared to non-treated controls.

The second column of data compares analgesic activity as demonstrated by ability to suppress the characteristic writhing induced in mice by 2-phenyl-1,4-benzoquinone [Proc. Soc. Exp. Biol. Med., 95, 729 (1957)]. The activity of several representative compounds of the present invention and of aspirin and phenylbutazone is expressed as $ED_{50}$, the dose (mg/kg) of compound producing a 50% reduction in the number of writhes as compared to non-treated 2-phenyl-1,4-benzoquinone dosed controls.

A common property of useful anti-inflammatory agents is their ability to lower elevated body temperatures. The third column of the data demonstrates the ability of the compounds of the present invention to reverse yeast-induced pyrexia in rats. Groups of ten female Charles River or Wistar rats (120–150 gm) are injected with a 20% water suspension of "Brewers Yeast" subcutaneously into the nape of the neck (10 ml/kg). The animals are starved (water ad lib.) and 18 hours later rectal temperatures are monitored (Tele-Thermometer, Yellow Springs Instrument Co., Inc., Yellow Springs, Ohio). Animals with a temperature ≥ 37.2°C. are considered fevered. Drugs are administered orally (10 ml/kg) using distilled water and, if insoluble, one drop of a dispersing agent, e.g. "Tween 80," per 10 ml. Temperatures are recorded 2 hours past drug. Significant activity is a reduction in rectal temperature ≥ 1° from the mean control temperature. The activity of the compounds tested is expressed as $ED_{50}$, the dose (mg/kg) of a compound producing a reduction of ≥ 1° in rectal temperature of fevered rats from the mean fevered control temperature in 50 percent of the animals.

A common but undesirable side effect of anti-inflammatory agents is the production of gastric irritation in mammals. The fourth column of data demonstrates that the compounds of the present invention show a low incidence of gastric irritation when tested in fasted rats. Groups of male or female rats (Wistar, Long Evans or Charles River), 150–180 gm, are utilized for this assay using 10 animals per dose group. The animals are starved for 48 hours ($H_2O$ ad lib) prior to administration of drug orally at 10 ml/kg. Drugs are prepared using distilled water solutions or, if insoluble, 1 drop of a dispersing agent, e.g. "Tween 80"/10 ml, is used with homogenization. The control group receives the vehicle only (10 ml/kg). For a time response, animals are treated with a highly active anti-inflammatory dose of the test compound, then sacrificed at 2, 3 and 5 hours or 3, 5 and 7 hours post drug. Stomachs are removed and examined for gastric irritation, which is defined as ulceration and/or hemorrhage of gastric mucosa. The presence of a single ulcer or hemorrhage spot is taken as positive and stomachs must be "clean" to be negative. A dose response is run at the peak time using at least four dose levels of test drug. In the table, gastric irritability is expressed as $ID_{50}$, the dose (mg/kg) of compound producing irritation in 50 percent of the animals after seven hours.

Table I

| Treatment | CARRAGEENIM PAW EDEMA-RATS $ED_{50}$ (mg/kg) | PHENYLQUINONE WRITHING-MICE $ED_{50}$ (mg/kg) | ANTIPYRETIC ASSAY-RATS $ED_{50}$ (mg/kg) | GASTRIC IRRITATION ASSAY-RATS $ID_{50}$ (mg/kg) |
|---|---|---|---|---|
| Aspirin | 130–140 | 53 | 35 | 42 |
| Phenylbutazone | 83 | 89 | <50 | 75 |
| 1-(3-carboxy-4-hydroxyphenyl)-2-phenyl-4,5,6,7-tetrahydroindole | 87 | 17 | 41 | 130 |
| 1-(3-carboxy-4-hydroxyphenyl)-2-phenyl-1,4,5,6-tetrahydrocyclopenta[b]pyrrole | 110 | 10 | <50 | 125 |
| 3-(3-carboxy-4-hydroxyphenyl)-4,5-dihydro-2-phenylbenz[3]indole | 63 | 10 | 69 | 300–350 |
| 1-(3-carboxy-4-hydroxyphenyl)-1,4,5,6,7,8-hexahydro-2-phenylcyclohepta[b]pyrrole | 125 | 10 | 100 | >200 |
| 3-(3-carboxy-4-hydroxyphenyl)-2-phenylbenz[e]indole | 90 | 16.5 | >100 | >200 |
| 1-(3-carboxy-4-hydroxyphenyl)-2-(4-fluorophenyl)-4,5,6,7-tetrahydroindole | 88 | — | — | — |
| 3-(4-acetoxy-3-carboxyphenyl)-4,5-dihydro-2-phenylbenz[e]indole | 70 | 16.5 | — | >300 |
| 1-(3-carboxy-4-mercaptophenyl)-2-phenyl-4,5,6,7-tetrahydroindole | 140 | — | — | — |

The compounds of the present invention also possess the ability to suppress adjuvant-induced arthritis in rats, another standard laboratory procedure to assess useful anti-inflammatory activity [D. T. Walz, M. M. Dolan, M. J. DiMartino, S. L. Yankell, Proc. Soc. Exp. Biol. & Med. 137, 1466 (1971)]. The efficacy of several representative compounds of the present invention and comparable data for aspirin and phenylbutazone, two commonly used anti-inflammatory agents in mammals is illustrated in Table II, where activity is indicated as percent decrease (at various doses) in inflammation compared to adjuvant treated controls.

Table II

| Treatment | Dose (mg/kg/day) | % Inhibition of Edema on Day 21 Adjuvant Injected Paw | Non-Injected Paw |
|---|---|---|---|
| Aspirin | 200 | 37 | 47 |
| Phenylbutazone | 50 | 60 | 71 |
| 1-(3-carboxy-4-hydroxyphenyl)-2-phenyl-4,5,6,7-tetrahydroindole | 100 | 65 | 80 |
|  | 50 | 38 | 72 |
| 1-(3-carboxy-4-hydroxyphenyl)-2-phenyl-1,4,5,6-tetrahydrocyclopenta[b]pyrrole | 100 | 57 | 75 |

Table II-continued

| Treatment | Dose (mg/kg/day) | % Inhibition of Edema on Day 21 Adjuvant Injected Paw | Non-Injected Paw |
|---|---|---|---|
| 3-(3-carboxy-4-hydroxyphenyl)-4,5-dihydro-phenylbenz[e]indole | 10<br>25<br>50 | 27<br>49<br>69 | 29<br>72<br>81 |
| 1-(3-carboxy-4-hydroxyphenyl)-1,4,5,6,7,8-hexahydro-2-phenyl-cyclopenta[b]pyrrole | 100 | 75 | 90 |
| 3-(3-carboxy-4-hydroxyphenyl)-2-phenylbenz[e]indole | 25<br>50 | 45<br>70 | 50<br>70 |
| 1-(3-carboxy-4-hydroxyphenyl)-2-(4-fluorophenyl)-4,5,6,7-tetrahydro-indole | 100 | 56 | 64 |
| 3-(4-acetoxy-3-carboxyphenyl)-4,5-dihydro-2-phenylbenz[e]indole | 50<br>100 | 56<br>82 | 68<br>93 |
| 1-(3-carboxy-4-mercaptophenyl)-2-phenyl-4,5,6,7-tetrahydroindole | 10<br>25<br>50 | 23<br>43<br>67 | 23<br>57<br>80 |

In summary, the data in Tables I and II show that the compounds of the present invention are effective anti-inflammatory agents in mammals at doses of from about 1 to about 200 mg/kg per day while displaying an unusual minimum of undesirable side effects.

The compounds of the present invention may be administered by any convenient route such as orally, intramuscularly, intravenously, subcutaneously, or interperitoneally. The preferred route of administration is oral, for example, with an inert diluent or with an edible carrier or in gelatin capsules or tablets. For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% of the weight of the unit. The amount of active compound in such compositions is such that a suitable dosage will be obtained. Preferred compositions and preparations according to the present invention are prepared so that an oral dosage unit form contains between 10 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or both. A syrup may contain, in addition to the active compounds, sucrose as a sweetening agent, and certain preservatives, dyes and colorings, and flavors. Materials used in preparing these various compositions must be pharmaceutically pure and non-toxic in the amounts utilized.

The following examples are representative of the compounds of the invention and their preparation. Temperatures are expressed in °C.

EXAMPLE 1 a. 2-Phenacyl-1-tetralone

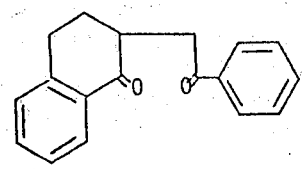

To a stirred refluxing solution of 20.2 g. (0.1 mole) of 1-(1-pyrrolidino)-3,4-dihydronaphthalene and 50 ml. of toluene was added dropwise during 30 minutes under nitrogen a solution of 20.1 g. (0.1 mole) of phenacyl bromide in 65 ml. of dry toluene. The mixture was heated under reflux for 6 hours, diluted with 50 ml. of water, refluxed for 4 hours, and cooled. The layers were separated and the aqueous phase was extracted with benzene. The organic solution was dried over sodium sulfate and concentrated to a semi-solid. Trituration with cold 30°–60° petroleum ether gave 23.6 g. (78%) of solid, m.p. 73°–76°. Recrystallization from 60°–90° petroleum ether raised the melting point to 87°–88°.

Calc. for $C_{18}H_{16}O_2$: 81.79% C; 6.10% H. Found: 81.19% C; 6.11% H.

b. 1-(3-Carboxyphenyl)-4,5-dihydro-2-phenylbenz[g]indole

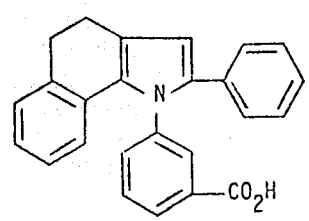

A solution of 10.5 g. (0.04 mole) of 2-phenacyl-1-tetralone (m.p. 73°–76°), 5.5 g. (0.04 mole) of m-aminobenzoic acid, and 35 ml. of glacial acetic acid was heated under reflux for 3½ hours, cooled and filtered. The filter cake was washed with water and dried to provide 8.6 g. of solid, m.p. 225°–228°. Recrystallization from ethanol and from ethanol-water gave off-white crystals, m.p. 253.5°–255°.

Calc. for $C_{25}H_{19}NO_2$: 82.17% C; 5.24% H; 3.83% N. Found: 81.51% C; 5.32% H; 3.80% N.

EXAMPLE 2

*a.* 2-Phenacylcyclohexanone

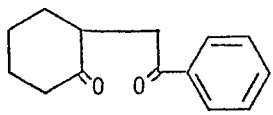

A solution of 60.9 g (0.31 mole) of phenacyl bromide in 150 ml. of toluene was added dropwise with stirring to a refluxing solution of 46.6 g. of 1-pyrrolidino-1-cyclohexene in 150 ml. of toluene. The mixture was heated under reflux for 2 hours, diluted with 150 ml. of water, refluxed for 3 hours and cooled. The layers were separated, and the aqueous phase was extracted with ether. The organic solution was dried and concentrated to an oil. Distillation gave 42.1 g. (64%) of orange liquid, b.p. 135°–141° (0.05 mm.), which solidified. Recrystallization from ether-petroleum ether gave tan crystals, m.p. 44°–45°.

Calc. for $C_{14}H_{16}O_2$: 77.78% C; 7.41% H. Found: 77.73% C; 7.53% H.

*b.* 1-(3-Carboxyphenyl)-2-phenyl-4,5,6,7-tetrahydroindole

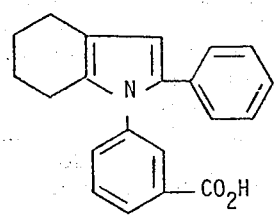

A solution of 10.8 g. (0.05 mole) of 2-phenacylcyclohexanone, 6.85 g. (0.05 mole) of m-aminobenzoic acid and 30 ml. of glacial acetic acid was heated under reflux for 6 hours, cooled and filtered. The filter cake was washed with water and recrystallized from ethanol to provide 5.7 g. (36%) of crystals, m.p. 191°–193°.

Calc. for $C_{21}H_{19}NO_2$: 79.50% C; 5.99% H; 4.42% N. Found: 79.16% C; 6.09% H; 4.40% N.

EXAMPLE 3

1-(2-Methoxycarbonylphenyl)-2-phenyl-4,5,6,7-tetrahydroindole

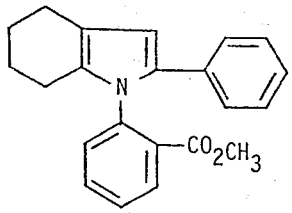

A solution of 10.8 g. (0.05 mole) of 2-phenacylcyclohexanone, 7.55 g. (0.05 mole) of methyl anthranilate, and 30 ml. of glacial acetic acid was heated under reflux for 7 hours, cooled, and diluted with water. The layers were separated, and the aqueous phase was extracted with ether. The combined organic phase was washed with sodium bicarbonate solution, dried over sodium sulfate, and concentrated to an oil. Chromatography on silica gel with toluene as the eluent gave 2.91 g. (18%) of a yellow oil.

Calc. for $C_{22}H_{21}NO_2$: 79.76% C; 6.34% H; 4.23% N. Found: 79.29% C; 6.54% H; 3.91% N.

EXAMPLE 4

1-(4-Carboxyphenyl)-2-phenyl-4,5,6,7-tetrahydroindole

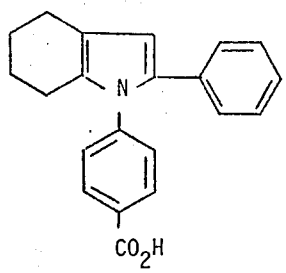

A solution of 10.8 g. (0.05 mole) of 2-phenacylcyclohexanone, 6.85 g. (0.05 mole) of p-aminobenzoic acid and 30 ml. of glacial acetic acid was heated under reflux for 5 hours and cooled. The solid which separated was collected and recrystallized from ethanol to provide 5.85 g. (37%) of pale yellow crystals, m.p. 244°–246°.

Calc. for $C_{21}H_{19}NO_2$: 79.50% C; 5.99% H; 4.42% N. Found: 79.30% C; 6.09% H; 4.53% N.

EXAMPLE 5

1-(3-Carboxy-4-hydroxyphenyl)-4,5-dihydro-2-phenylbenz[g]indole

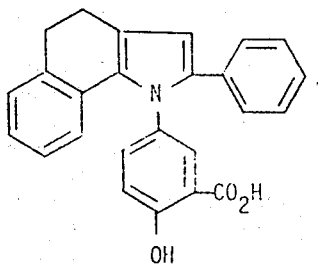

A mixture of 20.0 g. (0.076 mole) of 2-phenacyl-1-tetralone, 11.6 g. (0.076 mole) of 5-aminosalicylic acid, and 70 ml. of glacial acetic acid was heated under reflux for 4 hours, cooled diluted with 10 ml. of water and filtered. The filter cake was washed with water and dried to provide 15.5 g. of solid, m.p. 215°–218°. Recrystallization from benzene-cyclohexane gave 6.5 g. (22%) of yellow crystals, m.p. 245°–247°.

Calc. for $C_{25}H_{19}NO_3$: 78.72% C; 5.02% H; 3.67% N. Found: 79.02% C; 5.04% H; 3.47% N.

EXAMPLE 6

1-(4-Carboxy-3-hydroxyphenyl)-2-phenyl-4,5,6,7-tetrahydroindole

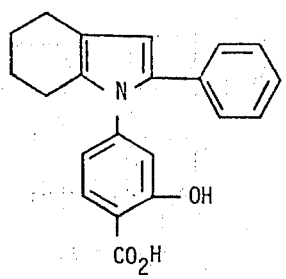

A solution of 32.4 g. (0.15 mole) of 2-phenacylcyclohexanone, 23.0 g. (0.15 mole) of 4-aminosalicylic acid and 90 ml. of glacial acetic acid was heated under reflux for 7 hours, cooled, diluted with 90 ml. of water and extracted with ether. The ether solution was dried over sodium sulfate and concentrated. The residue was recrystallized from benzene-ethanol to provide 3.36 g. (7%) of yellow crystals, m.p. 193°–195°.

Calc. for $C_{21}H_{19}NO_3$: 75.66% C; 5.74% H; 4.20% N. Found: 75.50% C; 5.81% H; 4.00% N.

EXAMPLE 7

1-(2-Carboxyphenyl)-4,5-dihydro-2-phenylbenz[g]indole

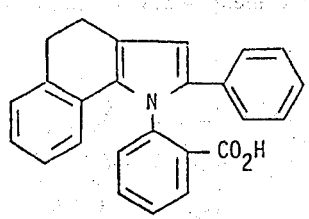

A mixture of 20.0 g. (0.076 mole) of 2-phenacyl-1-tetralone, 9.86 g. (0.072 mole) of anthranilic acid, and 70 ml. of glacial acetic acid was heated under reflux for 50½ hours and concentrated to an oil, which crystallized from isopropyl alcohol to provide 10.7 g. (41%) of solid, m.p. 170°–185°. Recrystallization from ethanol-water, isopropyl alcohol, and cyclohexane-methanol gave 4.0 g. of yellow crystals, m.p. 223.5°–224.5°.

Calc. for $C_{25}H_{19}NO_2$: 82.17% C; 5.24% H; 3.83% N. Found: 81.76% C; 5.30% H; 3.82% N.

EXAMPLE 8

1-(4-Dimethylphosphinylmethoxycarbonylphenyl)-4,5-dihydro-2-phenylbenz[g]indole

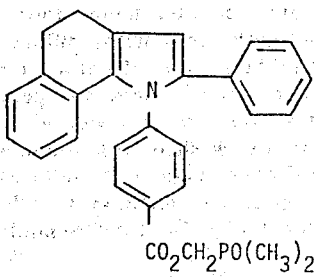

A mixture of 2.6 g. (0.01 mole) of 2-phenacyl-1-tetralone, 2.3 g. (0.01 mole) of dimethylphosphinylmethyl p-aminobenzoate, 0.4 g. of p-toluenesulfonic acid, and 250 ml. of dry toluene was heated under reflux for 73 hours, concentrated to about 100 ml., diluted with 25 ml. of cyclohexane, and cooled. The solid which separated was collected to provide 2.6 g. (57%) of solid, m.p. 171°–173°. Recrystallization from cyclohexane-benzene gave pale yellow crystals, m.p. 180°–181°.

Calc. for $C_{28}H_{26}NO_3P$: 73.83% C; 5.75% H; 3.08% N. Found: 73.75% C; 5.56% H; 2.94% N.

EXAMPLE 9

1-(3-Carboxy-4-hydroxyphenyl)-2-phenyl-4,5,6,7-tetrahydroindole

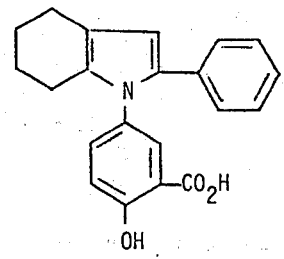

A solution of 49.7 g. (0.23 mole) of 2-phenacylcyclohexanone, 35.2 g. (0.23 mole) of 5-aminosalicylic acid, and 135 ml. of glacial acetic acid was heated under reflux under nitrogen for 3½ hours. A solid separated and was collected, washed with water, and recrystallized from acetic acid to provide 46.0 g. (60%) of pale yellow crystals, m.p. 209°–211°.

Calc. for $C_{21}H_{19}NO_3$: 75.66% C; 5.74% H; 4.20% N. Found: 75.61% C; 5.75% H; 4.30% N.

EXAMPLE 10

1-(3-Carboxy-4-methoxyphenyl)-2-phenyl-4,5,6,7-tetrahydroindole

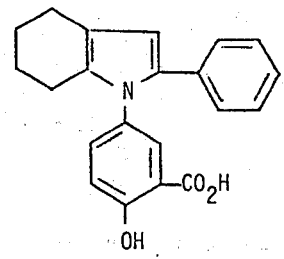

To a stirred mixture of 5.86 g. (0.018 mole) of 1-(3-carboxy-4-hydroxyphenyl)-2-phenyl-4,5,6,7-tetrahydroindole, 2.49 g. (0.044 mole) of powdered potassium hydroxide, and 50 ml. of acetone was added dropwise during 10 minutes at room temperature a solution of 5.31 g. (0.042 mole) of dimethyl sulfate in 15 ml. of acetone. After 3 hours, the solvent was removed under reduced pressure, the residue was suspended in water, and the mixture was extracted with ethyl acetate. The organic phase was washed with sodium bicarbonate solution, dried over magnesium sulfate, and concentrated to 6.3 g. of 1-(4-methoxy-3-methoxycarbonylphenyl)-2-phenyl-4,5,6,7-tetrahydroindole as an amber oil.

A mixture of this oil, 50 ml. of methanol, 20 ml. of water, and 2.13 g. (0.038 mole) of potassium hydroxide was heated under reflux for 2 hours, concentrated to about 50 ml., diluted with water, and acidified with hydrochloric acid. The solid which separated was collected and recrystallized from acetonitrile to provide 3.6 g. (51%) of crystals, m.p. 179°–189°.

Calc. for $C_{22}H_{21}NO_3$: 76.06% C; 6.09% H; 4.03% N. Found: 75.34% C; 6.08% H; 4.03% N.

EXAMPLE 11

1-(4-Acetoxy-3-carboxyphenyl)-2-phenyl-4,5,6,7-tetrahydroindole

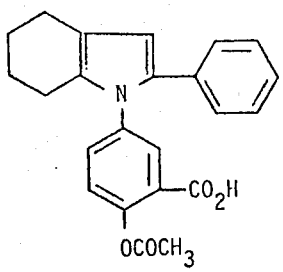

A mixture of 25.0 g. (0.075 mole) of 1-(3-carboxy-4-hydroxyphenyl)-2-phenyl-4,5,6,7-tetrahydroindole and 225 g. (2.25 mole) of acetic anhydride was heated under reflux for 3 hours, diluted with 200 ml. of tetrahydrofuran, and poured into 3 l. of water. An oil separated and slowly solidified. Recrystallization from acetic acid gave a tan solid, m.p. 155°–162°.

Calc. for $C_{23}H_{21}NO_4$: 73.58% C; 5.64% H; 3.73% N. Found: 73.37% C; 5.58% H; 3.78% N.

EXAMPLE 12

1-(4-Hydroxy-3-methoxycarbonylphenyl)-2-phenyl-4,5,6,7-tetrahydroindole

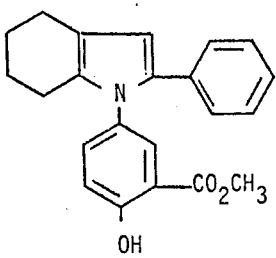

Hydrogen chloride gas was bubbled through a boiling mixture of 25.0 g. (0.075 mole) of 1-(3-carboxy-4-hydroxyphenyl) 2-phenyl-4,5,6,7-tetrahydroindole and 750 ml. of methanol for 2 hours. The mixture was heated under reflux for 18.5 hours, cooled and filtered to provide 19.6 g. (75%) of white solid. Recrystallization from methanol gave colorless crystals, m.p. 141°–142°.

Calc. for $C_{22}H_{21}NO_3$: 76.06% C; 6.09% H; 4.03% N. Found: 76.00% C; 6.03% H; 3.91% N.

EXAMPLE 13

1-(4-N,N-Dimethylthiocarbamoyloxy-3-methoxycarbonylphenyl)-2-phenyl-4,5,6,7-tetrahydroindole

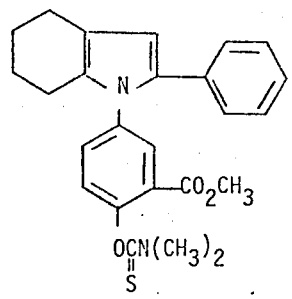

A mixture of 3.47 g. (0.01 mole) of 1-(4-hydroxy-3-methoxycarbonylphenyl)-2-phenyl-4,5,6,7-tetrahydroindole, 3.36 g. (0.03 mole) of 1,4-diazabicyclo[2.2.2]octane, 3.70 g. (0.03 mole) of N,N-dimethylthiocarbamoyl chloride, and 20 ml. of dry dimethyl formamide was heated at 60° for 2 hours, diluted with water, and extracted with benzene. The organic phase was washed with water, dried over sodium sulfate, and concentrated to an oil. Recrystallization from methanol gave 2.8 g. (65%) of colorless solid, m.p. 163°–164°.

Calc. for $C_{25}H_{26}N_2O_3S$: 69.10% C; 6.03% H; 6.45% N. Found: 69.28% C; 5.96% H; 6.35% N.

EXAMPLE 14

1-(4-N,N-Dimethylcarbamoylthio-3-methoxycarbonylphenyl)-2-phenyl-4,5,6,7-tetrahydroindole

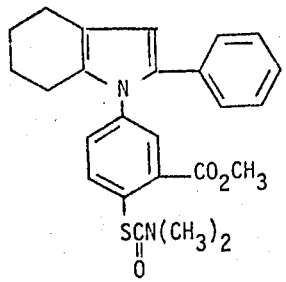

A 9.0 g. sample of 1-(4-N,N-dimethylthiocarbamoyloxy-3-methoxycarbonylphenyl)-2-phenyl-4,5,6,7-tetrahydroindole was heated for 2 hours at 220°–230°, cooled, and treated with isopropyl alcohol to provide 6.9 g. (77%) of yellow solid. Recrystallization from ether gave colorless crystals, m.p. 140°–141°.

Calc. for $C_{25}H_{26}N_2O_3S$: 69.10% C; 6.03% H; 6.45% N. Found: 68.95% C; 6.23% H; 6.37% N.

EXAMPLE 15

1-(3-Carboxy-4-mercaptophenyl)-2-phenyl-4,5,6,7-tetrahydroindole

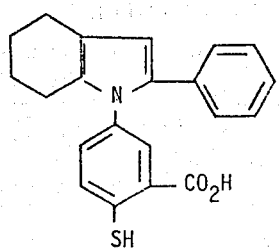

A mixture of 3.7 g. (0.009 mole) of 1-(4-N,N-dimethylcarbamoylthio-3-methoxycarbonylphenyl)-2-phenyl-4,5,6,7-tetrahydroindole, 2.4 g. (0.04 mole) of potassium hydroxide, 35 ml. of methanol and 10 ml. of water was heated under reflux for 3 hours, diluted with water, and acidified. The solid which separated was collected and recrystallized from acetic acid to provide 1.6 g. (54%) of colorless crystals, m.p. 186°–188°.

Calc. for $C_{21}H_{19}NO_2S$: 72.18% C; 5.48% H; 4.01% N. Found: 72.02% C; 5.56% H; 3.96% N.

EXAMPLE 16

1-(3-Carboxy-4-hydroxyphenyl)-2-phenylindole

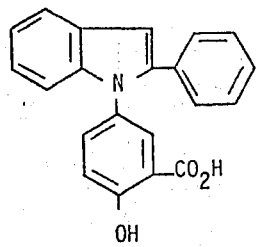

A mixture of 3.33 g. (0.01 mole) of 1-(3-carboxy-4-hydroxyphenyl)-2-phenyl-4,5,6,7-tetrahydroindole, 4.0 g. of 10% palladium on carbon, and 250 ml. of xylene was heated under reflux with stirring under nitrogen for 3 days, filtered, and concentrated to a solid. Trituration with cyclohexane afforded 2.4 g. (73%) of solid, m.p. 210°–212°. Recrystallization from acetic acid gave colorless crystals, m.p. 213.5°–214.5°.

Calc. for $C_{21}H_{15}NO_3$: 76.58% C; 4.59% H; 4.25% N. Found: 77.09% C; 4.62% H; 4.22% N.

EXAMPLE 17

1-(4-Acetoxy-3-carboxyphenyl)-2-phenylindole

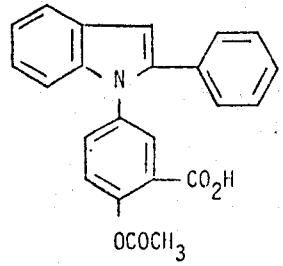

A mixture of 8.25 g. (0.025 mole) of 1-(3-carboxy-4-hydroxyphenyl)-2-phenylindole and 76.5 g. (0.75 mole) of acetic anhydride was heated under reflux for 1 hour, diluted with 75 ml. of tetrahydrofuran and poured into 1 l. of water. An oil separated, and during 2 days solidified. The solid was collected and recrystallized from acetonitrile to provide 4.8 g. (52%) of colorless crystals, m.p. 178°–180°.

Calc. for $C_{23}H_{17}NO_4$: 74.38% C; 4.62% H; 3.77% N. Found: 74.29% C; 4.91% H; 4.14% N.

EXAMPLE 18 a. 2-(p-Bromophenacyl)cyclohexanone

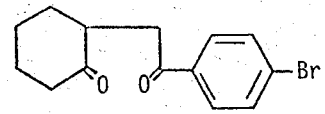

A suspension of 50 g. (0.18 mole) of p-bromophenacyl bromide in 215 ml. of toluene was added in small portions to a stirred boiling solution of 27.2 g. (0.18 mole) of 1-pyrrolidino-1-cyclohexene in 90 ml. of toluene. The mixture was heated under reflux for 2 hours, diluted with 90 ml. of water, and refluxed for 3 hours. The layers were separated and the aqueous phase was extracted with ether. The organic solution was dried over sodium sulfate and concentrated to an oil which solidified. Recrystallization from cyclohexane-ethanol gave 19.8 g. (37%) of colorless crystals, m.p. 78°–80°.

Calc. for $C_{14}H_{15}BrO_2$: 56.95% C; 5.08% H; 27.12% Br. Found: 56.88% C; 4.99% H; 27.37% Br.

b. 2-(4-Bromophenyl)-1-(3-carboxyphenyl)-4,5,6,7-tetrahydroindole

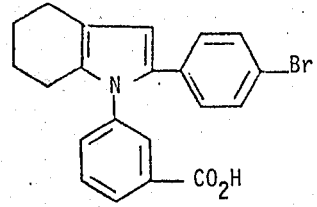

A mixture of 44.3 g. (0.15 mole) of 2-(p-bromophenacyl cyclohexanone, 20.6 g. (0.15 mole) of m-aminobenzoic acid, and 90 ml. of glacial acetic acid was heated under reflux for 5 hours, cooled and filtered to provide 13.8 g. (23%) of solid, m.p. 242°–244°. Recrystallization from ethanol-water gave crystals, m.p. 242°–243°.

Calc. for $C_{21}H_{18}BrNO_2$: 63.64% C; 4.55% H; 20.20% Br; 3.54% N. Found: 63.51% C; 4.66% H; 20.15% Br; 3.47% N.

EXAMPLE 19 a. 2-(m-Trifluoromethylphenacyl)cyclohexanone

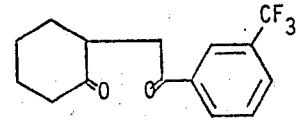

A stirred mixture of 15.9 g. (0.11 mole) of 1-pyrrolidino-1-cyclohexene, 28.0 g. (0.11 mole) of m-trifluoromethylphenacyl bromide, and 100 ml. of toluene was heated under reflux for 2 hours, diluted with water and refluxed for 2 hours. The layers were separated, and the organic phase was dried and concentrated to 25 g. of liquid. Distillation provided 12.0 g. (42%) of liquid, b.p. 137°–138° (0.075 mm.).

b.
1-(3-Carboxy-4-hydroxyphenyl)-2-(3-trifluoromethylphenyl)-4,5,6,7-tetrahydroindole

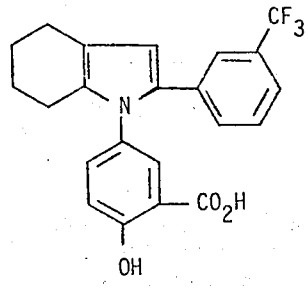

A mixture of 12.0 g. (0.042 mole) of 2-(m-trifluoromethylphenacyl)cyclohexanone, 6.45 g. (0.042 mole) of 5-aminosalicylic acid, and 30 ml. of glacial acetic acid was heated under reflux for 4 hours and filtered. The filtrate was diluted with water and the supernatant was decanted from the oil which separated. Trituration with cyclohexane gave 7.7 g. of solid, m.p. 215°–225°. Recrystallization from isopropyl alcohol-water afforded 4.1 g. (47%) of crystals, m.p. 223°–225°.

Calc. for $C_{22}H_{18}F_3NO_3$: 65.83% C; 4.52% H; 3.49% N. Found: 65.64% C; 4.71% H; 3.61% N.

EXAMPLE 20 a. 2-(p-Methoxyphenacyl)cyclohexanone

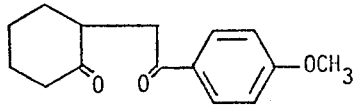

Reaction of 33.0 g. (0.22 mole) of 1-pyrrolidino-1-cyclohexene with 50.0 g. (0.22 mole) of p-methoxyphenacyl bromide by the method described in Example 2a gave 45 g. (84%) of crystal, m.p. 98°–99°.

b.
1-(3-Carboxy-4-hydroxyphenyl)-2-(4-methoxyphenyl)-4,5,6,7-tetrahydroindole

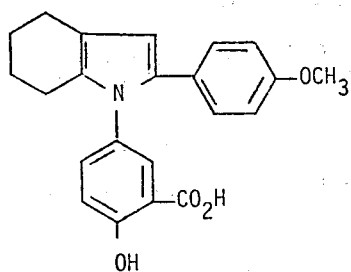

A mixture of 24.6 g. (0.1 mole) of 2-(p-methoxyphenacyl)cyclohexanone, 15.3 g. (0.1 mole) of 5-aminosalicylic acid, and 100 ml. of glacial acetic acid was heated under reflux for 3 hours, cooled and filtered. The filter cake was washed with water, dried and recrystallized from ethanol to provide 14.4 g. (40%) of crystals, m.p. 219°–221°.

Calc. for $C_{22}H_{21}NO_4$: 72.71% C; 5.82% H; 3.85% N. Found: 72.78% C; 5.87% H; 3.94% N.

EXAMPLE 21 a. 2-Phenacyl-cyclopentanone

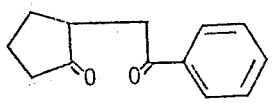

A solution of 72.4 g. (0.36 mole) of phenacyl bromide in 175 ml. of toluene was added dropwise during 30 minutes to a stirred, boiling solution of 50.0 g. (0.36 mole) of 1-pyrrolidino-1-cyclopentene and 200 ml. of toluene. The mixture was heated under reflux for 3 hours, diluted cautiously with 200 ml. of water, refluxed for 4 hours and cooled. The layers were separated, the aqueous phase extracted with benzene, and the combined organic phase was dried over sodium sulfate and concentrated to an oil. Distillation gave 24.8 g. (34%) of liquid, b.p. 138°–140° (0.05 mm.).

b.
1-(3-Carboxy-4-hydroxyphenyl)-2-phenyl-1,4,5,6-tetrahydrocyclopenta[b]pyrrole

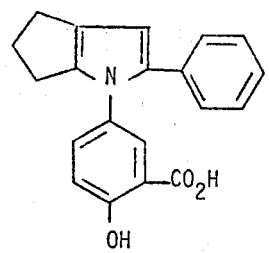

A mixture of 20.5 g. (0.1 mole) of 2-phenacylcyclopentanone, 15.3 g. (0.1 mole) of 5-aminosalicylic acid, and 60 ml. of glacial acetic acid was heated under reflux for 3 hours, cooled and filtered. The filter cake was washed with water, dried and recrystallized from acetic acid to provide 9.5 g. (30%) of crystals, m.p. 198°–199°.

Calc. for $C_{20}H_{17}NO_3$: 75.22% C; 5.37% H; 4.39% N. Found: 75.19% C; 5.40% H; 4.45% N.

EXAMPLE 22

2-(4-Bromophenyl)-1-(3-carboxy-4-hydroxyphenyl)-4,5,6,7-tetrahydroindole

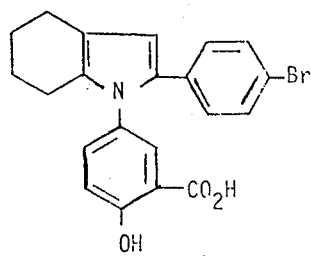

A mixture of 44.3 g. (0.15 mole) of 2-(p-bromophenacyl)cyclohexanone, 23.0 g. (0.15 mole) of 5-aminosalicylic acid, and 115 ml. of glacial acetic acid was heated under reflux for 2 hours, cooled and filtered. The filter cake was washed with water, dried and recrystallized from acetic acid to provide 11.9 g (19%) of tan crystals, m.p. 231°–232°.

Calc. for $C_{21}H_{18}BrNO_3$: 61.17% C; 4.37% H; 19.42% Br; 3.40% N. Found: 61.17% C; 4.27% H; 19.23% Br; 3.44% N.

EXAMPLE 23

1-(3-Carboxy-4-hydroxyphenyl)-2-(4-cyanophenyl)-4,5,6,7-tetrahydroindole

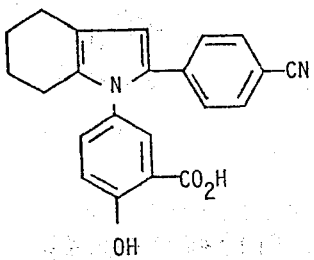

A mixture of 6.18 g. (0.015 mole) of 2-(4-bromophenyl)-1-(3-carboxy-4-hydroxyphenyl)-4,5,6,7-tetrahydroindole, 1.6 g. (0.018 mole) of cuprous cyanide, and 10 ml. of dimethyl formamide was heated under reflux for 6 hours, poured into a solution of 3 g. of sodium cyanide and 10 ml. of water, and after 5 minutes diluted with 46 ml. of water. The solution was acidified to pH 1–2 with hydrochloric acid and the solid which separated was collected. Recrystallization from acetic acid gave 1.21 g. (23%) of crystals, m.p. 242°–244°.

Calc. for $C_{22}H_{18}N_2O_3$: 73.73% C; 5.06% H; 7.82% N. Found: 72.89% C; 9.09% H; 7.73% N.

EXAMPLE 24 a. 1-Phenacyl-2-tetralone

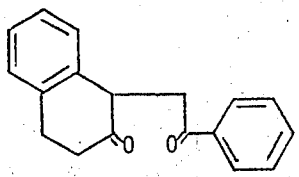

A solution of 20 g. (0.1 mole) of phenacyl bromide and 65 ml. of toluene was added during 30 minutes to a boiling, stirred solution of 20 g. (0.1 mole) of 1-(3,4-dihydro-2-naphthyl)pyrrolidine and 50 ml. of toluene. The mixture was heated under reflux for 3 hours, diluted with 50 ml. of water, refluxed for 4 hours and cooled. The layers were separated, the aqueous phase was extracted with benzene, and the organic solution was dried and concentrated to an oil. Crystallization from 30°–60°-petroleum ether-ether gave 16.7 g. (63%) of tan crystals, m.p. 48°–52°.

b. 3-(3-Carboxy-4-hydroxyphenyl)-4,5-dihydro-2-phenylbenz[e]indole

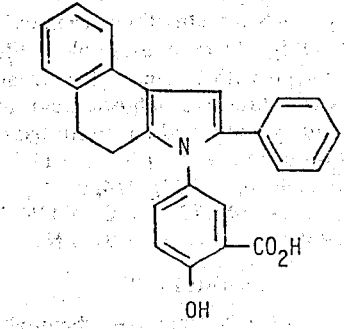

A mixture of 16.6 g. (0.063 mole) of 1-phenacyl-2-tetralone, 9.65 g. (0.063 mole) of 5-aminosalicylic acid, and 60 ml. of glacial acetic acid was heated under reflux under nitrogen for 2 hours, cooled and filtered. The collected solid was washed with acetic acid and water, dried and recrystallized from acetic acid to provide 16.3 g. (68%) of crystals, m.p. 223°–225°.

Calc. for $C_{25}H_{19}NO_3$: 78.72% C; 5.02% H; 3.67% N. Found: 78.58% C; 4.97% H; 3.73% N.

EXAMPLE 25

4,5-Dihydro-3-(4-hydroxy-3-methoxycarbonylphenyl)-2-phenylbenz[e]indole

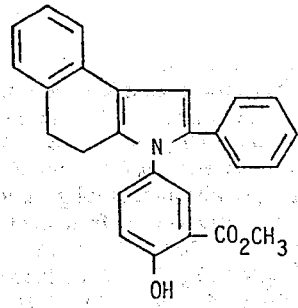

Hydrogen chloride gas was bubbled through a stirred, boiling mixture of 30.0 g. (0.08 mole) of 3-(3-carboxy-4-hydroxyphenyl)-4,5-dihydro-2-phenylbenz[e]indole and 790 ml. of methanol for 1 hour. The mixture was stirred under reflux for 6 hours, cooled and filtered to provide 28.4 g. (91%) of solid. Recrystallization from acetonitrile gave colorless crystals, m.p. 164.5°–165.5°.

Calc. for $C_{26}H_{21}NO_3$: 78.97% C; 5.35% H; 3.57% N. Found: 79.16% C; 5.47% H; 3.56% N.

EXAMPLE 26

4,5-Dihydro-3-(4-N,N-dimethylthiocarbamoyloxy-3-methoxycarbonylphenyl)-2-phenylbenz[e]indole

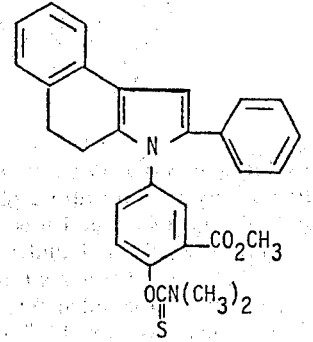

A mixture of 21.4 g. (0.054 mole) of 4,5-dihydro-3-(4-hydroxy-3-methoxycarbonylphenyl)-2-phenylbenz[e]indole, 18.3 g. (0.16 mole) of 1,4-diazabicyclo[2.2.2]octane, 100 ml. of dimethyl formamide, and 20.7 g. (0.16 mole) of N,N-dimethylthiocarbamoyl chloride was stirred at 60° for 45 minutes, cooled, diluted with water and extracted with benzene. The organic phase was washed with dilute hydrochloric acid and water, dried over sodium sulfate, and concentrated to a solid. Recrystallization from acetonitrile gave 11.7 g. (45%) of off-white crystals, m.p. 222°–224°.

Calc. for $C_{29}H_{26}N_2O_3S$: 72.17% C; 5.43% H; 5.81% N. Found: 72.45% C; 5.35% H; 5.97% N.

EXAMPLE 27

4,5-Dihydro-3-(4-N,N-dimethylcarbamoylthio-3-methoxycarbonylphenyl)-2-phenylbenz[e]indole

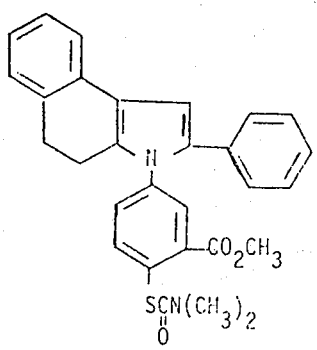

A 10.1 g. (0.021 mole) sample of 4,5-dihydro-3-(4-N,N-dimethylthiocarbamoyloxy-3-methoxycarbonylphenyl)-2-phenylbenz[e]indole was heated at 220°–225° under nitrogen for 50 minutes. Trituration of the resulting solid with methanol gave 9.5 g. (94%) of yellow solid. Recrystallization from acetonitrile gave off-white crystals, m.p. 203°–204.5°.

Calc. for $C_{29}H_{26}N_2O_3S$: 72.17% C; 5.43% H; 5.81% N. Found: 72.55% C; 5.33% H; 5.97% N.

EXAMPLE 28

4,5-Dihydro-3-(3-ethoxycarbonyl-4-hydroxyphenyl)-2-phenylbenz[e]indole

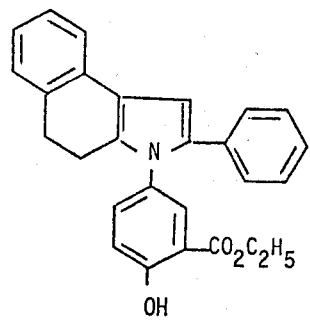

A boiling solution of 7.5 g. (0.02 mole) of 3-(3-carboxy-4-hydroxyphenyl)-4,5-dihydro-2-phenylbenz[e]indole and 200 ml. of ethanol was saturated with hydrogen chloride, then heated under reflux for 26 hours and cooled. The solid which separated was collected and recrystallized from ethanol to provide 4.1 g. (51%) of off-white crystals, m.p. 134°–135°.

Calc. for $C_{27}H_{23}NO_3$: 79.20% C; 5.66% H; 3.42% N. Found: 79.11% C; 5.70% H; 3.58% N.

EXAMPLE 29

1-Acetyl-3-(3-carboxy-4-hydroxyphenyl)-4,5-dihydro-2-phenylbenz[e]indole

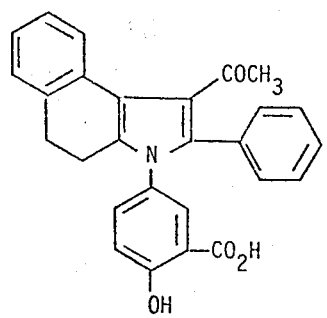

A mixture of 1.25 g. (0.0033 mole) of 3-(3-carboxy-4-hydroxyphenyl)-4,5-dihydro-2-phenylbenz[e]indole, 1 ml. of acetic anhydride, 10 ml. of glacial acetic acid, and 0.1 g. of p-toluenesulfonic acid was stirred at room termperature under nitrogen for 6 days. The solid which separated was collected, washed with acetic acid and petroleum ether, dried and recrystallized from methanol to provide 0.23 g (16%) of 3-(4-acetoxy-3-carboxyphenyl)-1-acetyl-4,5-dihydro-2-phenylbenz[e]indole. Concentration of the mother liquor, followed by recrystallization of the residue from ethanol-water, gave 0.25 g. (18%) of crystals, m.p. 223°–226°.

Calc. for $C_{27}H_{21}NO_3$: 76.58% C; 5.00% H; 3.31% N. Found: 76.29% C; 5.17% H; 3.26% N.

EXAMPLE 30

3-(4-Acetoxy-3-carboxyphenyl)-4,5-dihydro-2-phenylbenz[e]indole

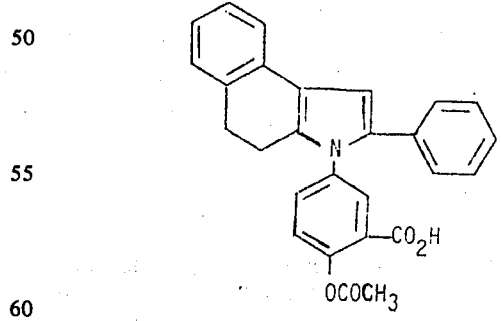

A mixture of 26.2 g. (0.069 mole) of 3-(3-carboxy-4-hydroxyphenyl)-4,5-dihydro-2-phenylbenz[e]indole and 204 g. of acetic anhydride was stirred at 75° for 4 hours, cooled, treated with 34 g. of water, stirred for several hours until a solution formed, and allowed to stand overnight. The solid which separated was collected, washed with acetic acid and petroleum ether, and dried to provide 26.7 g. (91%) of crystals, m.p. 194°–196°.

Calc. for $C_{27}H_{21}NO_4$: 76.58% C; 5.00% H; 3.31% N. Found: 76.42% C; 5.06% H; 3.21% N.

EXAMPLE 31

3-(3-Carboxy-4-hydroxyphenyl)-2-phenylbenz[e]indole

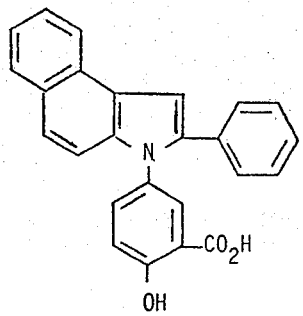

A mixture of 7.6 g. (0.02 mole) of 3-(3-carboxy-4-hydroxyphenyl)-4,5-dihydro-2-phenylbenz[e]indole, 9.1 g. of 10% palladium on carbon, and 350 ml. of xylene was heated under reflux with stirring under nitrogen for 24 hours and then filtered. The filtrate was concentrated to 135 ml. and cooled. The solid which separated was collected and recrystallized from xylene to provide 3.6 g. (48%) of yellow crystals, m.p. 241.5°–242.5°.

Calc. for $C_{25}H_{17}NO_3$: 79.14% C; 4.52% H; 3.69% N. Found: 79.76% C; 4.58% H; 3.76% N.

EXAMPLE 32 a. 2-(p-phenylphenacyl)cyclohexanone

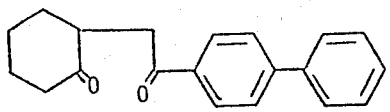

Reaction of 27.4 g. (0.18 mole) of 1-pyrrolidino-1-cyclohexene and 50 g. (0.18 mole) of p-phenylphenacyl bromide by the method described in Example 2a gave 23.6 g. (45%) of crystals, m.p. 108°–112°.

b.
2-(4-Biphenyl)-1-(3-carboxy-4-hydroxyphenyl)-4,5,6,7-tetrahydroindole

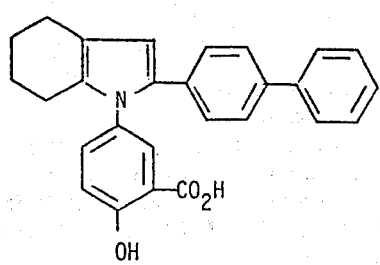

A mixture of 23.4 g. (0.08 mole) of 2-(p-phenylphenacyl)cyclohexanone, 12.2 g. (0.08 mole) of 5-aminosalicylic acid, and 80 ml. of glacial acetic acid was heated under reflux under nitrogen for 3 hours, cooled and filtered. The filter cake was washed with acetic acid and water, dried and recrystallized from acetic acid to provide 8.2 g. (22%) of crystals, m.p. 192°–199°.

Calc. for $C_{27}H_{23}NO_3$: 79.20% C; 5.66% H; 3.42% N. Found: 79.63% C; 5.68% H; 3.15% N.

EXAMPLE 33 a. 2-(m-Methoxyphenacyl)cyclohexanone

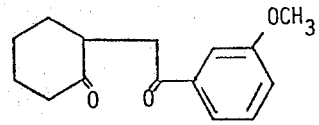

Reaction of 33 g. (0.22 mole) of 1-pyrrolidino-1-cyclohexene and 50 g. (0.22 mole) of m-methoxyphenacyl bromide by the method described in Example 2a gave 31.2 g. (58%) of an amber oil, b.p. 178°–182° (0.15 mm.)

b)
1-(3-Carboxy-4-hydroxyphenyl)-2-(3-methoxyphenyl)-4,5,6,7-tetrahydroindole

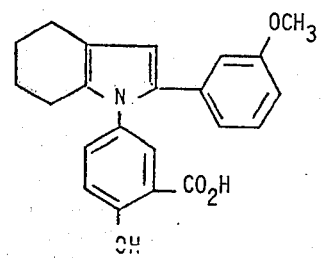

A mixture of 24.6 g. (0.1 mole) of 2-(m-methoxyphenacyl)cyclohexanone, 15.3 g. (0.1 mole) of 5-aminosalicylic acid, and 65 ml. of glacial acetic acid was heated for 2 hours under reflux under nitrogen and cooled. The solid which separated was collected, washed with acetic acid and water, dried and recystallized from acetic acid to provide 23.4 g. (65%) of crystals, m.p. 175°–177°.

Calc. for $C_{22}H_{21}NO_4$: 72.71% C; 5.82% H; 3.85% N. Found: 72.79% C; 5.80% H; 3.91% N.

EXAMPLE 34 a. 2-Phenacylcycloheptanone

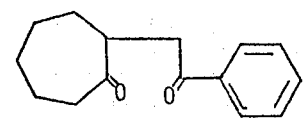

Reaction of 64.1 g. (0.4 mole) of 1-pyrrolidino-1-cycloheptene and 79.2 g. (0.4 mole) of phenacyl bromide by the method described in Example 2a gave 22.8 g. (25%) of tan crystals, m.p. 42°–44°.

b. 1-(3-Carboxy-4-hydroxyphenyl)-1,4,5,6,7,8-hexahydro-2-phenylcyclohepta[b]pyrrole

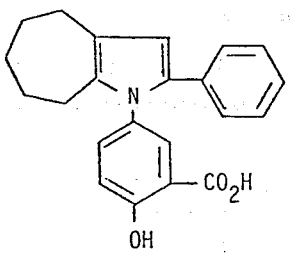

A mixture of 18.4 g. (0.08 mole) of 2-phenacylcycloheptanone, 12.1 g. (0.08 mole) of 5-aminosalicylic acid, and 140 ml. of glacial acetic acid was heated under reflux under nitrogen for 2 hours and cooled. The solid which separated was collected and recrystallized from ethanol to provide 16.5 (59%) of yellow crystals, m.p. 238°–239°. Calc. for $C_{22}H_{21}NO_3$: 76.08% C; 6.05% H; 4.03% N. Found: 75.72% C; 6.10% H; 4.18% N.

EXAMPLE 35 a. 2-(p-Chlorophenacyl)cyclohexanone

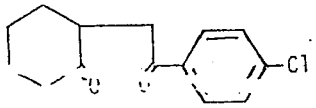

Reaction of 69.5 g. (0.46 mole) of 1-pyrrolidino-1-cyclohexene and 100 g. (0.46 mole) of p-chlorophenacyl bromide by the method described in Example 2a gave 82.4 g. (72%) of tan crystals, m.p. 56°–58° from ether-petroleum ether.

b. 1-(3-Carboxy-4-hydroxyphenyl)-2-(4-chlorophenyl)-4,5,6,7-tetrahydroindole

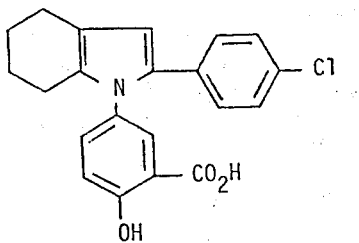

A mixture of 37.6 g. (0.15 mole) of 2-(p-chlorophenacyl)cyclohexanone, 23.0 g. (0.15 mole) of 5-aminosalicylic acid, and 215 ml. of glacial acetic acid was heated under reflux for 4 hours and cooled. The solid which separated was collected, washed with water and recrystallized from acetic acid and from ethanol to provide 26.2 (48%) of yellow crystals, m.p. 242°–243°.

Calc. for $C_{21}H_{18}ClNO_3$: 68.57% C; 4.90% H; 9.66% Cl; 3.81% N. Found: 68.65% C; 4.88% H; 9.56% Cl; 3.85% N.

EXAMPLE 36 a. 2-(o-Methoxyphenacyl)cyclohexanone

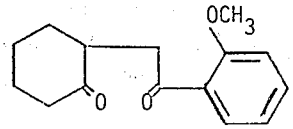

Reaction of 19.6 g. (0.13 mole) of 1-pyrrolidino-1-cyclohexene and 30.0 g. (0.13 mole) of o-methoxyphenacyl bromide by the method described in Example 2a gave 17.7 g. (55%) of a semi-solid.

b. 1-(3-Carboxy-4-hydroxyphenyl)-2-(2-methoxyphenyl)-4,5,6,7-tetrahydroindole

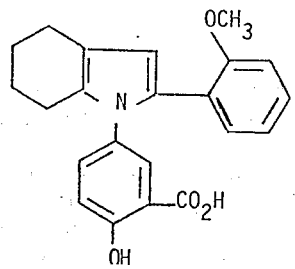

A mixture of 17.7 g. (0.072 mole) of 2-(o-methoxyphenacyl)cyclohexanone, 11.0 g. (0.072 mole) of 5-aminosalicylic acid, and 90 ml. of glacial acetic acid was heated under reflux for 4 hours and cooled. The solid which separated was collected, washed with water and recrystallized from ethanol to provide 0.2 (1%) of tan solid, m.p. 212°–214°.

Calc. for $C_{22}H_{21}NO_4$: 72.73% C; 5.79% H; 3.86% N. Found: 72.08% C; 5.69% H; 4.09% N.

EXAMPLE 37

2-Phenyl-1-(5-carboxy-4-hydroxy-2-trifluoromethylphenyl)-4,5,6,7-tetrahydroindole

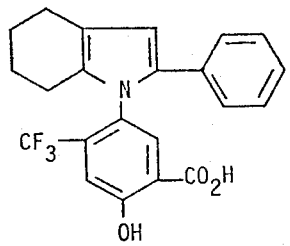

A mixture of 6.5 g. (0.029 mole) of 5-amino-4-trifluoromethylsalicylic acid, 6.35 g. (0.029 mole) of 2-phenacylcyclohexanone, and 30 ml. of glacial acetic acid was heated under reflux for 3 hours, cooled and filtered. The filter cake was recrystallized from acetic acid to provide 4.6 g. (39%) of gold crystals, m.p. 188°–190°.

Calc. for $C_{22}H_{19}F_3NO_3$: 65.83% C; 4.52% H; 3.49% N. Found: 65.90% C; 4.51% H; 3.54% N.

EXAMPLE 38

*a.* 2-(p-Fluorophenacyl)cyclohexanone

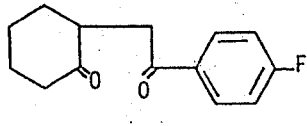

Reaction of 18.1 g. (0.12 mole) of 1-pyrrolidino-1-cyclohexene and 25.0 g. (0.12 mole) of p-fluorophenacyl bromide by the method described in Example 2a gave 17.9 g. (64%) of solid.

*b.*
1-(3-Carboxy-4-hydroxyphenyl)-2-(4-fluorophenyl)-4,5,6,7-tetrahydroindole

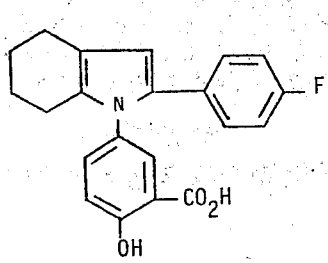

A solution of 17.9 g. (0.077 mole) of 2-(p-fluorophenacyl)cyclohexanone, 11.8 g. (0.077 mole) of 5-aminosalicylic acid, and 90 ml. of glacial acetic acid was heated under reflux under nitrogen for 4¾ hours, cooled and filtered. The collected solid was washed with water and recrystallized from acetic acid to provide 10.0 g. (37%) of yellow crystals, m.p. 239°–240°.

Calc. for $C_{21}H_{18}FNO_3$: 71.79% C; 5.13% H; 5.47% F; 3.99% N. Found: 70.83% C; 5.09% H; 4.92% F; 3.92% N.

EXAMPLE 39

*a.* 2-(p-Methylphenacyl)cyclohexanone

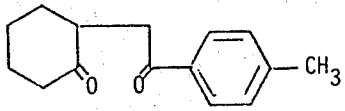

A solution of 50 g. (0.23 mole) of p-methylphenacyl bromide in 120 ml. of dry dimethyl formamide was added dropwise during ½ hour into a stirred, cooled solution of 35.4 g. (0.23 mole) of 1-pyrrolidino-1-cyclohexene in 200 ml. of dimethyl formamide at a rate to maintain a temperature of 25°. After 5½ hours, the solution was diluted with water and extracted with chloroform. The chloroform solution was washed with water, dried over sodium sulfate and concentrated to an oil. Distillation gave 28.5 g. (53%) of liquid, b.p. 161°–165° (0.2 mm.), which solidifed (m.p. 65°–70°).

*b.*
1-(3-Carboxy-4-hydroxyphenyl)-2-(4-methylphenyl)-4,5,6,7-tetrahydroindole

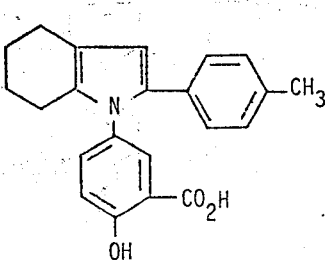

A mixture of 23 g. (0.1 mole) of 2-(p-methylphenacyl)cyclohexanone, 15.3 g. (0.1 mole) of 5-aminosalicylic acid and 100 ml. of glacial acetic acid was heated under reflux for 45 minutes, cooled and filtered. The collected solid was recrystallized from acetonitrile to provide 23.0 g. (66%) of yellow crystals, m.p. 212.5°–214.5°.

Calc. for $C_{22}H_{21}NO_3$: 76.06% C; 6.09% H; 4.03% N. Found: 76.03% C; 6.13% H; 3.98% N.

EXAMPLE 40

*a.* 4-(t-Butyl)-2-phenacylcyclohexanone

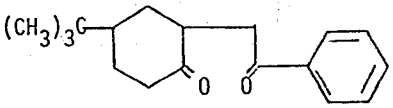

Reaction of 61.0 g. (0.30 mole) of 4-(t-butyl)-1-cyclohexene and 59.7 g. (0.30 mole) of phenacyl bromide by the method described in Example 39a provided 31.7 g. (39%) of solid, m.p. 127°–129° from ethanol.   *b.*   5-(t-Butyl)-1-(3-carboxy-4-hydroxyphenyl)-2-phenyl-4,5,6,7-tetrahydroindole

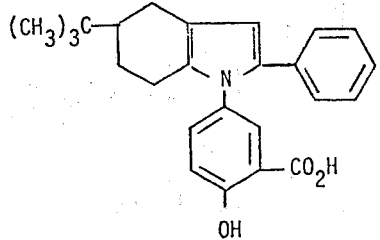

A solution of 20.0 g. (0.074 mole) of 4-(t-butyl)-2-phenacylcyclohexanone, 11.3 g. (0.074 mole) of 5-aminosalicylic acid, and 132 ml. of glacial acetic acid was heated under reflux under nitrogen for 2 hours, cooled and filtered. The collected solid was recrystallized from acetonitrile to provide 19.9 g. (69%) of crystals, m.p. 260°–262°.

Calc. for $C_{25}H_{27}NO_3$: 77.12% C; 6.94% H; 3.60% N. Found: 76.90% C; 6.99% H; 3.64% N.

EXAMPLE 41

5-(t-Butyl)-1-(3-carboxy-4-hydroxyphenyl)-2-phenylindole

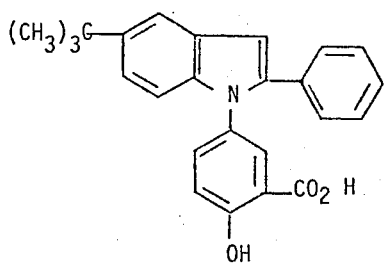

A mixture of 16 g. (0.041 mole) of 5-(t-butyl)-1-(3-carboxy-4-hydroxyphenyl)-2-phenyl-4,5,6,7-tetrahydroindole, 8 g. of 10% palladium on carbon, and 1.6 l. of xylene was heated under reflux under nitrogen for 23 hours and filtered. The filtrate was concentrated to 400 ml., cooled and filtered to provide 13.0 g. (82%) of crystals, m.p. 275°–276°. Recrystallization from acetonitrile gave crystals, m.p. 271°–273°.

Calc. for $C_{25}H_{23}NO_3$: 77.90% C; 6.01% H; 3.63% N. Found: 78.42% C; 6.09% H; 3.86% N.

EXAMPLE 42

*a.* 1(3,3-Dimethyl-2-oxobutyl)-2-tetralone

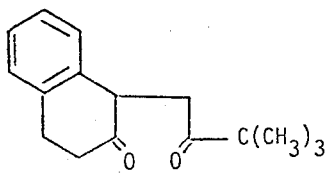

Raction of 17.9 g. (0.1 mole) of 1-bromo-3,3-dimethyl-2-butanone and 19.9 g. (0.01 mole) of 1(3,4-dihydro-2-naphthyl)pyrrolidine by the method described in Example 39a gave 15.6 g. (64%) of liquid, b.p. 149°–151° (0.07 mm.).

*b.*
2-(t-Butyl)-3-(3-carboxy-4-hydroxyphenyl)-4,5-dihydrobenz[e]indole

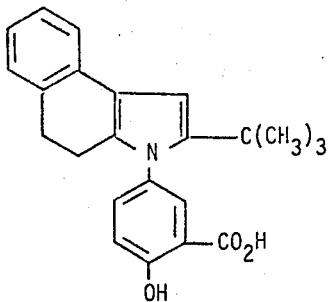

A mixture of 15.2 g. (0.062 mole) of 1-(3,3-dimethyl-2-oxobutyl)-2-tetralone, 9.5 g. (0.062 mole) of 5-aminosalicylic acid, and 50 ml. of glacial acetic acid was heated under reflux under nitrogen for 1.5 hours, cooled and filtered. The collected solid was washed with acetic acid and petroleum ether and then recrystallized from acetonitrile to provide 10.4 g. (46%) of off-white crystals, m.p. 258°–260°.

Calc. for $C_{23}H_{23}NO_3$: 76.43% C; 6.41% H; 3.88% N. Found: 76.38% C; 6.39% H; 4.02% N.

EXAMPLE 43

1-(3-Carboxy-5-chloro-4-hydroxyphenyl)-2-phenyl-4,5,6,7-tetrahydroindole

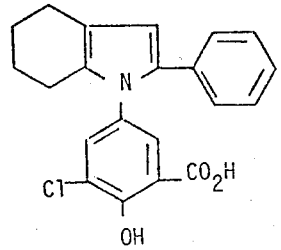

a mixture of 10.3 g. (0.047 mole) of 2-phenacylcyclohexanone, 8.8 g. (0.047 mole) of 5-amino-3-chlorosalicylic acid, and 45 ml. of glacial acetic acid was heated under reflux for 1 hour, cooled and filtered. The collected solid was recrystallized from acetonitrile to provide 13.3 g. (77%) of crystals, m.p. 223°–225°.

Calc. for $C_{21}H_{18}ClNO_3$: 68.57% C; 4.93% H; 3.81N. Found: 68.62% C; 4.90% H; 3.83% N.

EXAMPLE 44

*a.* 2-(p-Hydroxyphenacyl)cyclohexanone

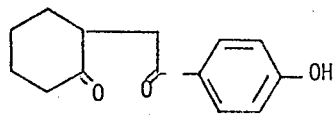

Reaction of 43 g. (0.2 mole) of p-hydroxyphenacyl bromide and 30 g. (0.2 mole) of 1-pyrrolidino- 1-cyclohexene by the method described in Example 39a gave 28 g. (61%) of solid, m.p. 120°–125°.

*b.*
1-(3-Carboxy-4-hydroxyphenyl)-2-(4-hydroxyphenyl)-4,5,6,7-tetrahydroindole

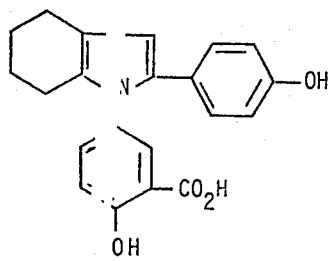

A mixture of 11.5 g. (0.05 mole) of 2-(p-hydroxyphenacyl)cyclohexanone, 7.6 g. (0.05 mole) of 5-aminosalicylic acid, and 40 ml. of glacial acetic acid was heated under reflux under nitrogen for 1.5 hours, cooled and filtered to provide 10.6 g. (61%) of solid, m.p. 214°–217°. Recrystallization from acetonitrile gave crystals, m.p. 217°–219°.

Calc. for $C_{21}H_{19}NO_4$: 72.19% C; 5.48% H; 4.01% N. Found: 72.16% C; 5.50% H; 4.37% N.

EXAMPLE 45

*a* 4-Methyl-2-phenacylcyclohexanone

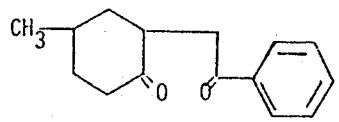

Reaction of 72.5 g. (0.44 mole) of 4-methyl-1-pyrrolidino-1-cyclohexene and 87.6 g. (0.44 mole) of phenacyl bromide by the method described Example 39*a* gave 75.3 g. (74%) of viscous oil.

*b.*
1-(3-Carboxy-4-hydroxyphenyl)-5-methyl-2-phenyl-4,5,6,7-tetrahydroindole

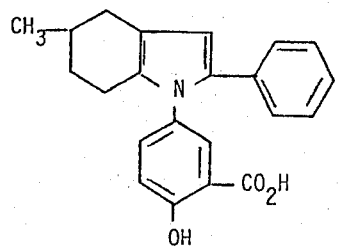

a solution of 50 g. (0.22 mole) of 4-methyl-2-phenacylcyclohexanone, 33.7 g. (0.22 mole) of 5-aminosalicylic acid, and 257 ml. of glacial acetic acid was heated under reflux for 3 hours, cooled and filtered. The collected solid was washed with water and recrystallized from acetonitrile to provide 43.3 g. (57%) of yellow crystals, m.p. 213°–215°.

Calc. for $C_{22}H_{21}NO_3$: 76.08% C; 6.05% H; 4.03% N.
Found: 75.73% C; 6.16% H; 4.05% N.

EXAMPLE 46

1-(4-Acetamido-3-carboxyphenyl)-2-phenyl-4,5,6,7-tetrahydroindole

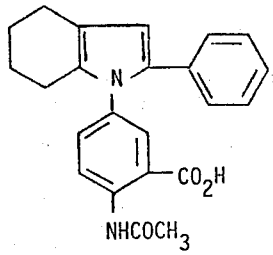

A mixture of 11.7 g. (0.054 mole) of 2-phenacylcyclohexanone, 10.5 g. (0.054 mole) of 2-acetamido-5-aminobenzoic acid, and 50 ml. of glacial acetic acid was heated under reflux for 4 hours, cooled, diluted with 15 ml. of methanol and filtered. The collected solid was recrystallized from acetonitrile to provide 9.45 g. (47%) of crystals, m.p. 192°-194°.

Calc. for $C_{23}H_{22}N_2O_3$: 73.78% C; 5.92% H; 7.48% N.
Found: 73.56% C; 5.96% H; 7.56% N.

EXAMPLE 47

1-(4-Amino-3-carboxyphenyl)-2-phenyl-4,5,6,7-tetrahydroindole

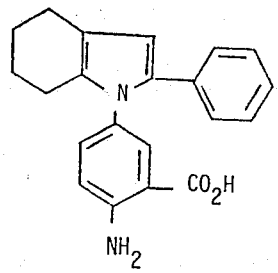

A mixture of 4.0 g. (0.011 mole) of 1-(4-acetamido-3-carboxyphenyl)-2-phenyl-4,5,6,7-tetrahydroindole, 50 ml. of ethanol, 10 ml. of water, and 2 ml. of conc. hydrochloric acid was heated under reflux under nitrogen for 4 hours, concentrated to 10 ml., diluted with 100 ml. of water, adjusted to pH 4 and filtered. Recrystallization of the collected solid from 75% ethanol gave 0.83 g. (23%) of crystals, m.p. 205.5°–206.5°.

Calc. for $C_{21}H_{20}N_2O_2$: 75.88% C; 6.06% H; 8.43% N.
Found: 75.85% C; 6.01% H; 8.45% N.

EXAMPLE 48

1-(5-Acetamido-3-carboxy-4-hydroxyphenyl)-2-phenyl-4,5,6,7-tetrahydroindole

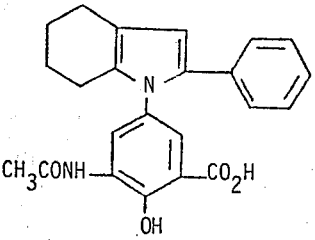

A mixture of 10.3 g. (0.048 mole) of 2-phenacylcyclohexanone, 10 g. (0.048 mole) of 3-acetamido-5-aminosalicylic acid, and 70 ml. of glacial acetic acid was heated under reflux under nitrogen for 1 hour, cooled and filtered. Recrystallization of the collected solid from acetic acid gave 10.5 g. (57%) of crystals, m.p. 232°–234°.

Calc. for $C_{23}H_{22}N_2O_4$: 70.75% C; 5.68% H; 7.17% N.
Found: 70.54% C; 5.74% H; 7.32% N.

EXAMPLE 49

1-(5Bromo-3-carboxy-4-hydroxyphenyl)-2-phenyl-4,5,6,7-tetrahydroindole

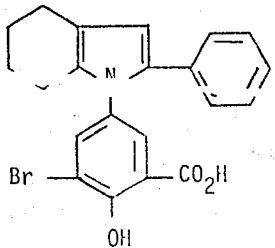

A mixture of 8.1 g. (0.038 mole) of 2-phenacylcyclohexanone, 8.7 g. (0.038 mole) of 5-amino-3-bromosalicylic acid, and 50 ml. of glacial acetic acid was heated under reflux for 1 hour, cooled and filtered. Recrystallization of the collected solid from acetonitrile gave 7.0 g. (46%) of yellow crystals, m.p. 209°–210°.

Calc. for $C_{21}H_{18}BrNO_3$: 61.17% C; 4.40% H; 3.40% N. Found: 61.03% C; 4.48% H; 3.46% N.

EXAMPLE 50 a 4-Methoxy-2-phenacylcyclohexanone

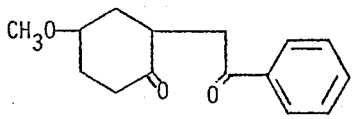

Reaction of 61.4 g. (0.31 mole) of phenacyl bromide and 55.7 g. (0.31 mole) of 4-methoxy-1-pyrrolidino-1-cyclohexene by the method described in Example 39a gave 68.0 g. (90%) of an amber oil.

b.
1-(3-carboxy-4-hydroxyphenyl)-5-methoxy-2-phenyl-4,5,6,7-tetrahydroindole

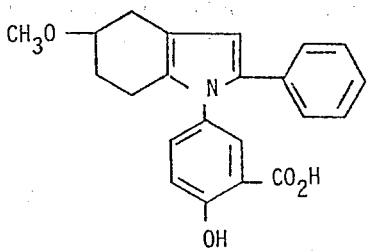

A mixture of 24.6 g. (0.1 mole) of 4-methoxy-2-phenacylcyclohexanone, 15.3 g. (0.1 mole) of 5-aminosalicylic acid, and 80 ml. of glacial acetic acid was heated under reflux for 1.5 hours, filtered, cooled and again filtered. The collected solid was washed with acetic acid and petroleum ether and recrystallized from acetonitrile to provide 22.5 g. (62%) of crystals, m.p. 207°–210°.

Calc. for $C_{22}H_{21}NO_4$: 72.71% C; 5.82% H; 3.85% N. Found 72.60% C; 5.89% H; 4.09% N.

EXAMPLE 51 a. 2-(3,4-Dichlorophenacyl)cyclohexanone

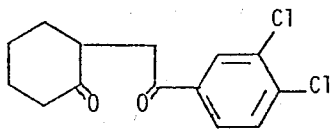

Reaction of 28.7 g. (0.19 mole) of 1-pyrrolidino-1-cyclohexene and 51.2 g. (0.19 mole) of 3,4-dichlorophenacyl bromide by the method described in Example 39a gave 32.6 g. (60%) of crystals, m.p. 78°–79° (from ethanol).

b.
1-(3-Carboxy-4-hydroxyphenyl)-2-(3,4-dichlorophenyl)-4,5,6,7-tetrahydroindole

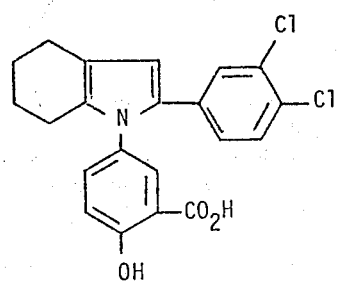

A solution of 15 g. (0.05 mole) of 2-(3,4-dichlorophenacyl)cyclohexanone, 7.7 g. (0.05 mole) of 5-aminosalicylic acid, and 63 ml. of glacial acetic acid was heated under reflux under nitrogen for 1½ hours, cooled and filtered. The collected solid was washed with water and recrystallized from acetonitrile to provide 19.4 g. (97%) of yellow crystals, m.p. 210°–211°.

Calc. for $C_{21}H_{17}Cl_2NO_3$: 62.69% C; 4.23% H; 17.66% Cl; 3.48% N. Found: 62.81% C; 4.33% H; 17.78% Cl; 3.62% N.

EXAMPLE 52 a. 2-(p-Bromophenacyl)cyclopentanone

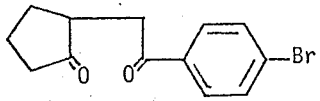

Reaction of 24.7 g. (0.18 mole) of 1-pyrrolidino-1-cyclopentene and 50 g. (0.18 mole) of p-bromophenacyl bromide by the method described in Example 39a gave 20.8 g. (41%) of crystals, m.p. 59°–61° (from ethanol).

b.
2-(4-Bromophenyl)-1(3-carboxy-4-hydroxyphenyl)-1,4,5,6-tetrahydrocyclopenta[b]pyrrole

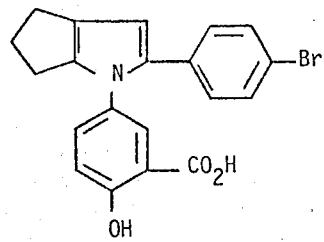

A solution of 20.8 g. (0.07 mole) of 2-(p-bromophenacyl)cyclopentanone, 10.71 g. (0.07 mole) of 5-aminosalicylic acid, and 88 ml. of glacial acetic acid was heated under reflux under nitrogen for 3½ hours, cooled and filtered. The collected solid was chromatographed on silica gel. The solid eluted with benzene was recrystallized from ethanol-water to provide tan crystals, m.p. 215°–216°.

Calc. for $C_{20}H_{16}BrNO_3$: 60.30% C; 4.02% H; 20.10% Br; 3.52% N. Found: 59.70% C; 4.02% H; 20.24% Br; 3.43% N.

EXAMPLE 53

1-(3-Carboxy-4-chloropheny)-2-phenyl-4,5,6-tetrahydroindole

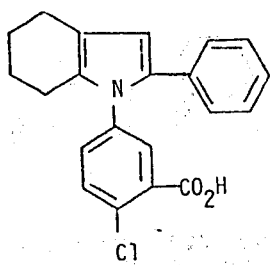

A mixture of 21.6 g. (0.1 mole) of 2-phenacylcyclohexanone, 17.2 g. (0.1 mole) of 5-amino-2-chlorobenzoic acid, and 60 ml. of glacial acetic acid was heated under reflux for 2 hours, cooled and filtered to provide 15.3 g. (44%) of light pink solid. Recrystallization from acetonitrile gave pale pink crystals, m.p. 210°–212°.

Calc. for $C_{21}H_{18}ClNO_2$: 71.69% C; 5.16% H; 3.98% N. Found: 71.13% C; 5.31% H; 4.26% N.

EXAMPLE 54 a. 2-(α-Phenylphenacyl)cyclohexanone

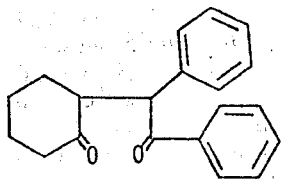

Reaction of 75.0 g. (0.5 mole) of 1-pyrrolidino-1-cyclohexane and 68.7 g. (0.25 mole) of α-phenylphenacyl bromide by the method described in Example 39a gave 73 g. of colorless semi-solid.

b.
1-(3-Carboxy-4-hydroxyphenyl)-2,3-diphenyl-4,5,6,7-tetrahydroindole

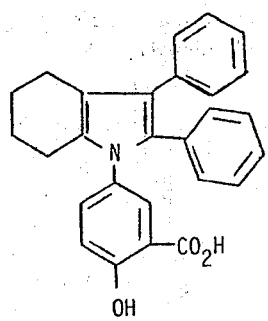

A solution of 10.5 g. (0.036 mole) of 2-(α-phenylphenacyl)cyclohexanone, 5.5 g. (0.036 mole) of 5-aminosalicylic acid, and 40 ml. of glacial acetic acid was heated under reflux for 1 ⅔ hours, cooled and filtered. The collected solid was washed with petroleum ether and recrystallized from acetonitrile to provide 7.3 g. (50%) of pale yellow crystals, m.p. 246°–247°.

Calc. for $C_{27}H_{23}NO_3$: 79.20% C; 5.66% H; 3.42% N. Found: 79.10% C; 5.92% H; 3.52% N.

EXAMPLE 55 a. 2-(p-Nitrophenacyl)cyclohexanone

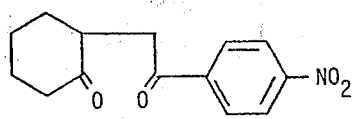

Reaction of 52.9 g. (0.35 mole) of 1-pyrrolidino-1-cyclohexene and 85.0 g. (0.35 mole) of p-nitrophenacyl bromide by the method described in Example 39a gave 81.3 g. (89%) of crystals, m.p. 61°–63° (from ethanol).

b.
1-(3-Carboxy-4-hydroxyphenyl)-2-(4-nitrophenyl)-4,5,6,7-tetrahydroindole

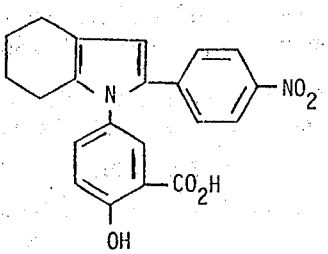

A mixture of 40 g. (0.15 mole) of 2-(p-nitrophenacyl)cyclohexanone, 23 g. (0.15 mole) of 5-aminosalicylic acid and 187 ml. of glacial acetic acid was heated under reflux under nitrogen for 3 ¾ hours, diluted with water and extracted with ethyl acetate. The ethyl acetate solution was dried over sodium sulfate and concentrated to a red solid which was chromatographed on silica gel. The material eluted with 3% methanol in chloroform was recrystallied from acetonitrile to provide 3.8 g. (7%) of orange crystals, m.p. 241°–242°.

Calc. for $C_{21}H_{18}N_2O_5$: 66.67% C; 4.76% H; 7.41% N. Found: 66.60% C; 4.88% H; 7.69% N.

EXAMPLE 56 a. 6-Methoxy-1-phenacyl-2-tetralone

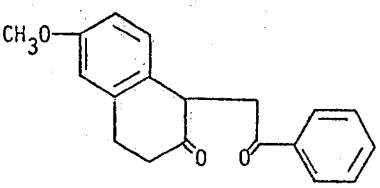

Reaction of 6.5 g. (0.0028 mole) of 3,4-dihydro-6-methoxy-2-pyrrolidinonapthalene and 5.7 g. (0.29 mole) of phenacyl bromide by the method described in Example 39a gave 6.0 g. (67%) of tan crystals, m.p. 55°–59°.

b.
3-(3-Carboxy-4-hydroxyphenyl)-4,5-dihydro-7-methoxy-2-phenylbenz[e]indole

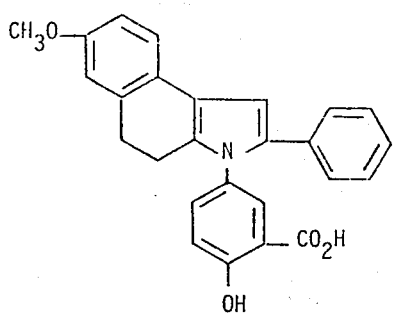

A mixture of 5.8 g. (0.02 mole) of 6-methoxy-1-phenacyl-2-tetralone, 3.02 g. (0.02 mole) of 5-aminosalicylic acid, and 20 ml. of glacial acetic acid was heated under reflux for 1 hour, cooled, and filtered. The collected solid was washed with acetic acid and petroleum ether and recrystallized from acetonitrile to provide 5.3 g (67%) of pale yellow crystals, m.p. 233°–234°.

Calc. for $C_{26}H_{21}NO_4$: 75.90% C; 5.14% H; 3.40% N. Found: 76.43% C; 5.28% H; 3.53% N.

EXAMPLE 57 a. 6-Chloro-1-phenacyl-2-tetralone

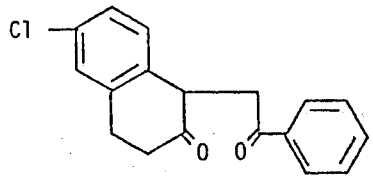

Reaction of 28.0 g. (0.12 mole) of 6-chloro-3,4-dihydro-2-pyrrolidinonaphthalene and 24.0 g. (0.12 mole) of phenacyl bromide by the method described in Example 39a gave 10.1 g. (28%) of brown oil.

b.
3-(3-Carboxy-4-hydroxyphenyl)-7-chloro-4,5-dihydro-2-phenylbenz[e]indole

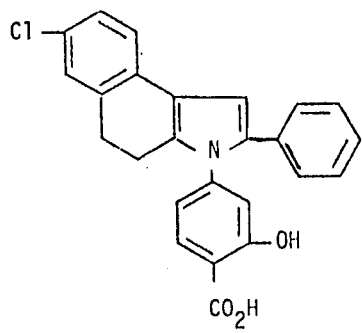

A mixture of 10.1 g. (0.03 mole) of 6-chloro-1-phenacyl-2-tetralone, 4.5 g. (0.03 mole) of 5-aminosalicylic acid and 30 ml. of glacial acetic was heated under reflux for 70 minutes, cooled and filtered. The collected solid was washed with acetic acid and petroleum ether and recrystallized from acetonitrile to give 4.3 g. (59%) of colorless crystals, m.p. 249°–251°.

Calc. for $C_{25}H_{18}ClNO_3$: 72.20% C; 4.36% H; 3.37% N. Found: 71.84% C; 4.50% H; 3.41% N.

EXAMPLE 58 a. 1-Phenacyl-2-indanone

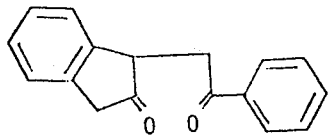

Reaction of 58.1 g. (0.29 mole) of phenacyl bromide and 54 g (0.29 mole) of 2-pyrrolidinoindene by the method described in Example 39a gave 7 g. of a viscous oil.

b.
1-(3-Carboxy-4-hydroxyphenyl)-1,8-dihydro-2-phenylindeno[2,1-b]pyrrole

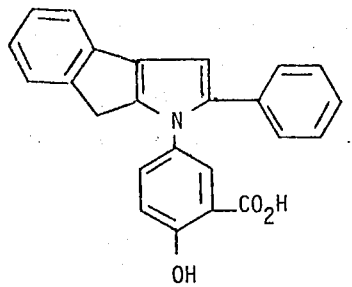

A mixture of 4.0 g. (0.016 mole) of 1-phenacyl-2-indanone, 2.45 g. (0.016 mole) of 5-aminosalicylic acid and 10 ml. of glacial acetic acid was heated under reflux under nitrogen for 2 hours, cooled and filtered. The collected solid was washed with petroleum ether and recrystallized from acetic acid to provide 4.6 g. (78%) of yellow crystals, m.p. 201°–205°.

Calc. for $C_{24}H_{17}NO_3$: 78.46% C; 4.66% H; 3.81% N. Found: 78.31% C; 4.65% H; 3.73% N.

EXAMPLE 59

1-(3-Carboxy-4-hydroxyphenyl)-4,5,6,7-tetrahydro-2-(2-thienyl)indole

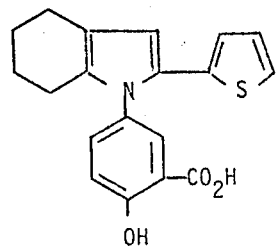

A mixture of 2.22 g. (0.01 mole) of 2-(2-thienoylmethyl)cyclohexanone, (1.53 g. (0.01 mole) of 5-aminosalicylic acid, and 25 ml. of ethanol was heated uder reflux under nitrogen for 4 hours and filtered. The filtrate was concentrated to an oil which solidified when triturated with petroleum ether. Recrystallization from acetonitrile gave 1.0 g. (29%) of yellow crystals, m.p. 211°–213°.

Calc. for $C_{19}H_{17}NO_3S$: 67.23% C; 5.05% H; 4.13% N. Found: 67.23% C; 4.98% H; 4.14% N.

EXAMPLE 60

3-(3-Carbamoyl-4-hydroxyphenyl)-4,5-dihydro-2-phenylbenz[e]indole

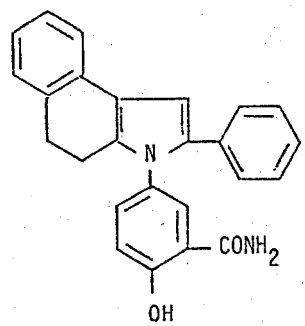

A mixture of 2.0 g. (0.005 mole) of 4,5-dihydro-3-(4-hydroxy-3-methoxycarbonylphenyl)2-phenylbenz[e]indole, 75 ml. of ammonium hydroxide, and 40 ml. of dimethyl formamide was heated under reflux for 3 hours, cooled, diluted with water, acidified, and extracted with ether. The ether phase was dried over sodium sulfate and concentrated to a solid. Recrystallization from benzene gave 1.21 g. (63%) of colorless crystals, m.p. 213°–215°.

Calc. for $C_{25}H_{20}N_2O_2$: 78.92% C; 5.31% H; 7.36% N. Found: 78.61% C; 5.31% H; 7.18% N.

EXAMPLE 61

4,5-Dihydro-3-(3-N-ethylcarbamoyl-4-hydroxyphenyl)-2-phenylbenz[e]indole

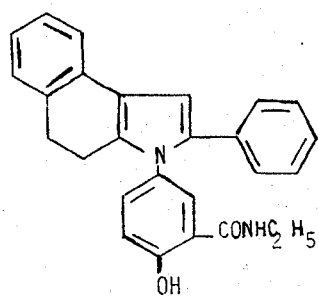

A mixture of 5.0 g. (0.013 mole) of 4,5-dihydro-3-(4-hydroxy-3-methoxycarbonylphenyl)-2-phenylbenz[e]indole, 70 ml. of ethyl amine, and 30 ml. of water was stirred at room temperature for 18 hours, diluted with water, acidified to pH 2, and filtered. The collected solid was recrystallized from hexane to provide 2.9 g. (56%) of colorless crystals, m.p. 175°–176°.

Calc. for $C_{27}H_{24}N_2O_2$: 79.39% C; 5.92% H; 6.86% N. Found: 79.44% C; 5.99% H; 6.83% N.

EXAMPLE 62

3-(3-N,N-Diethylcarbamoyl-4-hydroxyphenyl)-4,5-dihydro-2-phenylbenz[e]indole

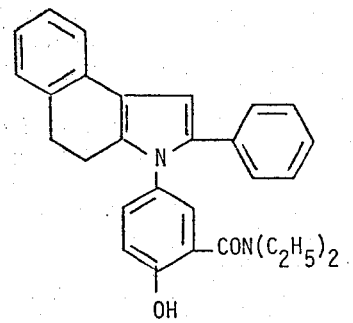

A mixture of 1.0 g. (0.0025 mole) of 4,5-dihydro-3-(4-hydroxy-3-methoxycarbonylphenyl)-2-phenylbenz[e]indole, 0.15 g. (0.0028 mole) of sodium methoxide, 5 ml. of diethylamine, and 20 ml. of methanol was stirred at room temperature for 3 days, diluted with water, acidified and filtered to provide 1.0 g. (92%) of off-white crystals, m.p. 235°–237°.

EXAMPLE 63

4,5-Dihydro-3-(3-N-hydroxycarbamoyl-4-hydroxyphenyl)-2-phenylbenz[e]indole

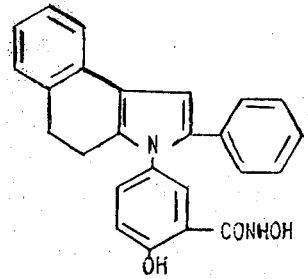

A solution of 1.4 g. (0.02 mole) of hydroxylamine hydrochloride, 1.03 g. (0.02 mole) of sodium methoxide, and 20 ml. of methanol was added to a stirred suspension of 4.0 g. (0.01 mole) of 4,5-dihydro-3-(4-hydroxy-3-methoxycarbonylphenyl)-2-phenylbenz[e]indole in 30 ml. of methanol. The mixture was diluted with 25 ml. of water and 50 ml. of methanol, heated under reflux for 24 hours, acidified, and extracted with chloroform. The chloroform solution was dried over magnesium sulfate and concentrated to a red solid. Recrystallization from benzene and then from acetonitrile gave yellow crystals, m.p. 115°–120°.

EXAMPLE 64

3-(3-Carboxy-4-mercaptophenyl)-4,5-dihydro-2-phenylbenz[e]indole

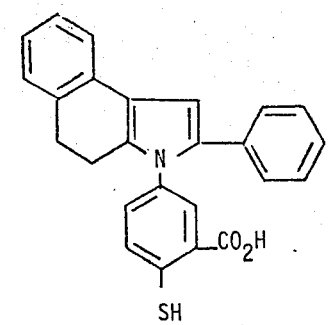

A mixture of 4.0 g. (0.0083 mole) of 4,5-dihydro-3-(4-dimethylcarbamoylthio-3-methoxycarbonylphenyl-2-phenylbenz[e]indole, 2.4 g. of potassium hydroxide, 35 ml. of methanol, and 10 ml. of water was heated under reflux for 3 hours, diluted with water, acidified, and filtered. The collected solid was recrystallized from aqueous acetone to provide 2.1 g. (62%) of yellow crystals, m.p. 260°–262°.

Calc. for $C_{25}H_{19}NO_2S$: 75.57% C; 4.78% H; 3.53% N. Found: 75.63% C; 4.84% H; 3.38% N.

We claim:

1. An orally administerable composition for treating inflammation and pain which consists essentially of a pharmaceutically acceptable carrier and from about 1 to about 200 mg of an active compound of the formula

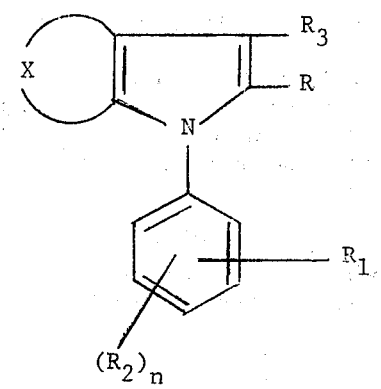

wherein

R is alkyl of one to six carbon atoms; thienyl; phenyl; diphenyl; or phenyl substituted by halogen, trifluoromethyl, alkyl of one to six carbon atoms, alkoxy of one to six carbon atoms, nitro, cyano, or hydroxy;

$R_1$ is carboxyl, alkoxycarbonyl of two to seven carbon atoms, carbamoyl, N-alkylcarbamoyl of two to seven carbon atoms, N,N-dialkylcarbamoyl of three to seven carbon atoms, hydroxycarbamoyl, or dialkylphosphinylalkoxycarbonyl of four to ten carbon atoms;

$R_2$ is hydrogen, hydroxyl, mercapto, halogen, trifluoromethyl, alkoxy of one to six carbon atoms, alkanoyloxy of one to six carbon atoms, amino, alkanoylamino of one to six carbon atoms, dialkylthiocarbamoyloxy of three to seven carbon atoms, or dialkylcarbamoylthio of three to seven carbon atoms; n is 1 or 2;

$R_3$ is hydrogen, alkanoyl of one to six carbon atoms, or phenyl;

X is alkylene of three to five carbon atoms, alkylene of three to five carbon atoms substituted by alkyl or alkoxy of one to six carbon atoms, divinylene, divinylene substituted by alkyl of one to six carbon atoms,

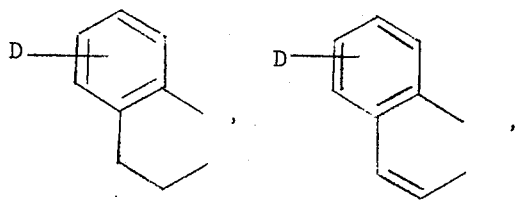

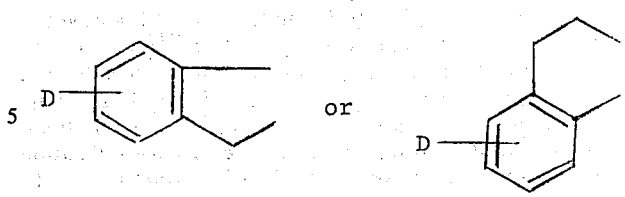

wherein D is hydrogen, alkoxy of one to six carbon atoms, or halogen.

2. An orally administerable composition for treating inflammation and pain which consists essentially of a pharmaceutically acceptable carrier and from about 1 to about 200 mg of an active compound as defined in claim 1 in which R is tertiary butyl, thienyl, phenyl, diphenyl or phenyl substituted by chlorine, bromine, fluorine, hydroxyl, trifluoromethyl, methyl, methoxy, nitro or cyano;

$R_1$ is carboxyl, methoxycarbonyl, ethoxycarbonyl, carbamoyl, N-ethylcarbamoyl, N,N-diethylcarbamoyl, hydroxycarbamoyl, or dimethylphosphinylmethoxycarbonyl;

$R_2$ is hydrogen, hydroxyl, mercapto, chlorine, bromine, trifluoromethyl, methoxy, acetyl, acetylamino, dimethylthiocarbamoyloxy or dimethylcarbamoylthio;

$R_3$ is hydrogen, acetyl, or phenyl; and

X is alkylene of three to five carbon atoms, butylene substituted by methyl, tertiary butyl or methoxy, divinylene, divinylene substituted by tertiary butyl,

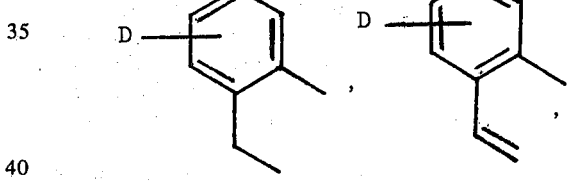

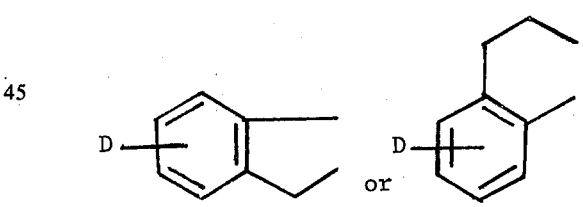

wherein D is hydrogen, methoxy or chlorine.

3. A composition as defined in claim 2 in which the active compound is 3-(3-carboxy-4-hydroxyphenyl)-4,5-dihydro-2-phenylbenz[e]indole.

4. A composition as defined in claim 2 in which the active compound is 3-(4-acetoxy-3-carboxyphenyl)-4,5-dihydro-2-phenylbenz[e]indole.

5. A composition as defined in claim 2 in which the active compound is 3-(3-carboxy-4-hydroxyphenyl)-2-phenylbenz[e]indole.

6. A composition as defined in claim 2 in which the active compound is 1-(3-carboxy-4-hydroxyphenyl)-2-phenylindole.

7. A composition as defined in claim 2 in which the active compound is 1-)3-carboxy-4-hydroxyphenyl)-2-phenyl-4,5,6,7-tetrahydroindole.

8. A composition as defined in claim 2 in which the active compound is 1-(3-carboxy-4-mercaptophenyl)-2-phenyl-4,5,6,7-tetrahydroindole.

9. A composition as defined in claim 2 in which the active compound is 1-(3-carboxy-4-hydroxyphenyl)-2-(4-fluorophenyl)-4,5,6,7-tetrahydroindole.

10. A composition as defined in claim 2 in which the active compound is 1-(3-carboxy-4-hydroxyphenyl)-2-phenyl-1,4,5,6-tetrahydrocyclopenta[b]pyrrole.

11. A composition as defined in claim 2 in whichh the actice compound is 1-(3-carboxy-4-hydroxyphenyl)-1,4,5,6,7,8-hexahydro-2-phenycyclohepta[b]pyrrole.

12. A composition as defined in claim 2 in which the active compound is 1-(3-carboxy-4-mercaptophenyl)-2-phenyl-4,5,6,7-tetrahydroindole.

13. A method of treating inflammation and pain which comprises administering to a patient an effective amount from about 1 to about 200 mg/kg per doz of an active compound of the formula

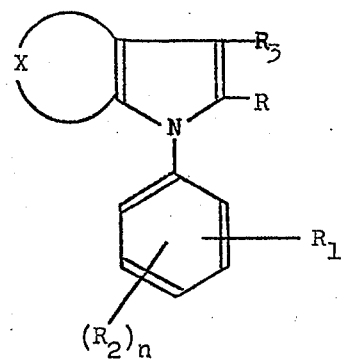

wherein
R is alkyl of one to six carbon atoms; thienyl; phenyl; diphenyl; or phenyl substituted by halogen, trifluoromethyl alkyl of one to six carbon atoms, alkoxy of one to six carbon atoms, nitro, cyano, or hydroxy;

$R_1$ is carboxyl, alkoxycarbonyl of two to seven carbon atoms, carbamoyl, N-alkylcarbamoyl of two to seven carbon atoms, N,N,-dialkylcarbamoyl of three to seven carbon atoms, hydroxycarbamoyl, or dialkylphosphinylalkoxycarbonyl of four to 10 carbon atoms;

$R_2$ is hydrogen, hydroxyl, mercapto, halogen, trifluoromethyl, alkoxy of one to six carbon atoms, alkanoyloxy of one to six carbon atoms, amino, alkanoylamino of one to six carbon atoms, dialkylthiocarbamoyloxy of three to seven carbon atoms, or dialkylcarbamoylthio of three to seven carbon atoms; $n$ is 1 to 2;

$R_3$ is hydrogen, alkanoyl of one to six caron atoms, or phenyl;

X is alkylene of three to five carbon atoms, alkylene of three to five carbon atoms substituted by alkyl or alkoxy of one to six carbon atoms, divinylene, divinylene substituted by alkyl of one to six carbon atoms,

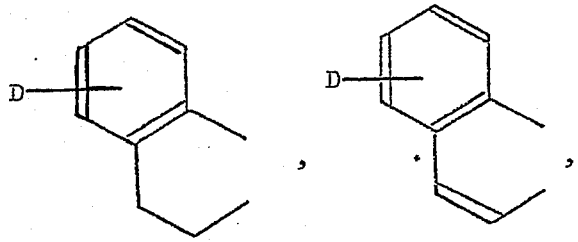

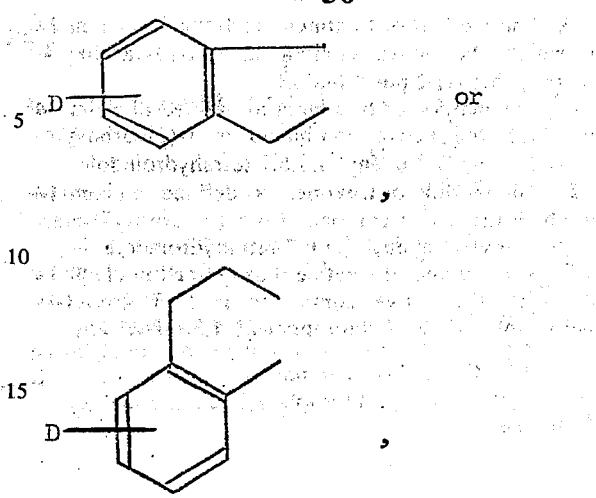

wherein D is hydrogen, alkoxy of one to six carbon atoms, or halogen.

14. A method of treatment as defined in claim 13 wherein R is tertiary butyl, thienyl, phenyl, diphenyl or phenyl substituted by chlorine, bromine, fluorine, hydroxyl, trifluoromethyl, methyl, methoxy, nitro or cyano;

$R_1$ is carboxyl, methoxycarbonyl, ethoxycarbonyl, carbamoyl, N-ethylcarbamoyl, N,N-diethylcarbamoyl, hydroxycarbamoyl or dimethylphosphinylmethoxycarbonyl;

$R_2$ is hydrogen, hydroxyl, mercapto, chlorine, bromine, trifluoromethyl, methoxy, acetyl, acetylamino, dimethylthiocarbamoyloxy or dimethylcarbamoylthio;

$R_3$ is hydrogen, acetyl, or phenyl; and

X is alkylene of three to five carbon atoms, butylene substituted by methyl, tertiary butyl or methoxy, divinylene, divinylene substituted by tertiary butyl,

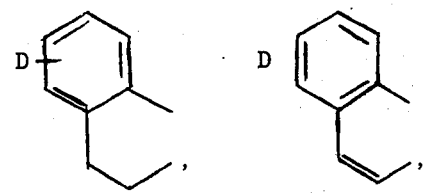

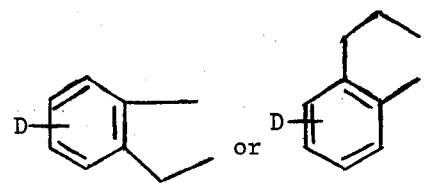

wherein D is hydrogen, methoxy or chlorine.

15. The method of treatment as defined in claim 14 in which the active compound is 3-(3-carboxy-4-hydroxyphenyl)-4, 5-dihydro-2-phenylbenz[e]indole.

16. The method of treatment as defined in claim 14 in which the active compound is 3-(4-acetoxy-3-carboxyphenyl)-4, 5-dihydro-2-phenylbenz[e]indole.

17. The method of treatment as defined in claim 14 in which the active compound is 3-(3-carboxy-4-hydroxyphenyl)-2-phenylbenz[e]indole.

18. The method of treatment as defined in claim 14 in which the active compound is 1-(3-carboxy-4-hydroxyphenyl)-2-phenylindole.

19. The method of treatment as defined in claim 14 in which the active compound is 1-(3-carboxy-4-hydroxyphenyl)-2-phenyl-4,5,6,7-tetrahydroindole.

20. The method of treatment as defined in claim 14 in which the active compound is 1-(3-carboxy-4-mercaptophenyl)-2-phenyl-4,5,6,7-tetrahydroindole.

21. The method of treatment as defined in claim 14 in which the active compound is 1-(3-carboxy-4-hydroxyphenyl)-2-(4-fluorophenyl)-4,5,6,7-tetrahydroindole.

22. The method of treatment as defined in claim 14 in which the active compound is 1-(3-carboxy-4-hydroxyphenyl)-2-phenyl-1,4,5,6-tetrahydrocyclopenta[b]pyrrole.

23. The method of treatment is defined in claim 14 in which the active compound is 1-(3-carboxy-4-hydroxyphenyl)-1,4,5,6,7,8-hexahydro-2-phenylcyclohepta[b]pyrrole.

24. The method of treatment as defined in claim 14 in which the active compound is 1-(3-carboxy-4-mercaptophenyl)-2-phenyl-4,5,6,7-tetrahydroindole.

* * * * *

UNITED STATES PATENT AND TRADEMARK OFFICE
CERTIFICATE OF CORRECTION

PATENT NO. : 3,931,407
DATED : January 6, 1976
INVENTOR(S) : Richard C. Allen, et al It is certified that error appears in the above-identified patent and that said Letters Patent are hereby corrected as shown below:

Column 12, Table I; in the heading: "CARRAGEENIM" should be -- CARRAGEENIN --

Column 13, Table II; (line 7): "dihydro-phenylbenz" should be -- dihydro-2-phenylbenz- --

Column 25, line 42: "9.09%H" should be - -5.09%H - -

Column 34, line 27: "76.03%C" should be - -76.30%C - -

Column 35, line 38: "Raction" should be - - Reaction - -

Column 36, line 19: "a" should be - -A- -

Column 36, line 25: "3.81N" should be - -3.81%N- -

Column 37, line 33: "a" should be - -A- -

Column 38, line 56: "1-(5Bromo. . ." should be - -1-(5-Bromo. . .

Column 41, line 10: "chloropheny)" should be - -chlorophenyl)- - and "4,5,6-tetra" should be 4,5,6,7-tetra- -

Column 43, line 1: "0.0028" should be - -0.028- -

Column 43, line 2: "napthalene" should be - -naphthalene- -

Column 44, line 2: "4.5g" should be - -4.6 g- -

Column 46, line 41: "1.03g" should be - -1.08g - -

Claim 7; line 2: "1-)3-" should be - -1-(3- --

UNITED STATES PATENT AND TRADEMARK OFFICE
CERTIFICATE OF CORRECTION

PATENT NO. : 3,931,407
DATED : January 6, 1976
INVENTOR(S) : Richard C. Allen, et al It is certified that error appears in the above-identified patent and that said Letters Patent are hereby corrected as shown below:

Claim 11; line 1: "whichh" should be - -which- -;

Claim 11; line 2: "actice" should be - -active- -

Claim 13; line 3: "doz" should be - -day- -;

Claim 13 (Column 49, line 52): "1 to 2" should be - - 1 or 2 - -

Signed and Sealed this first Day of June 1976

[SEAL]

Attest:

RUTH C. MASON
Attesting Officer

C. MARSHALL DANN
Commissioner of Patents and Trademarks